United States Patent [19]

Rector et al.

[11] Patent Number: 5,023,334
[45] Date of Patent: Jun. 11, 1991

[54] ANTHELMINTIC PYRIDINYL ACYLHYDRAZONES

[75] Inventors: Douglas L. Rector, Oshtemo Township; George A. Conder, Richland Township; Sylvester D. Folz, Comstock Township, all of Kalamazoo County, Mich.

[73] Assignee: The Upjohn Company, Kalamazoo, Mich.

[21] Appl. No.: 402,385

[22] Filed: Sep. 1, 1989

Related U.S. Application Data

[63] Continuation of Ser. No. 934,575, Oct. 3, 1986, which is a continuation-in-part of Ser. No. 715,425, Mar. 25, 1985, abandoned, which is a continuation-in-part of Ser. No. 700,375, Feb. 11, 1985, abandoned.

[51] Int. Cl.$^5$ .................... C07D 405/6; C07D 213/40; C07D 213/55; C07D 213/77
[52] U.S. Cl. .................... 546/268; 546/291; 546/332; 546/333; 546/335
[58] Field of Search ................ 546/332, 333, 268, 291

[56] References Cited

U.S. PATENT DOCUMENTS 4,974,485  1/1990  Farooq ................ 546/264

*Primary Examiner*—Alan L. Rotman
*Attorney, Agent, or Firm*—William G. Jameson

[57] ABSTRACT

This invention concerns a process for killing internal parasites, especially nematodes and cestodes affecting warm blooded animals such as sheep, cattle, swine, goats, dogs, cats, horses and humans as well as poultry by administering an effective amount of a compound of the Formula I:

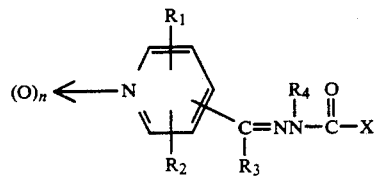

Certain of the compounds of Formula I are novel and in further embodiments of the invention provide novel compounds and compositions for use in the process of the invention. The compounds are readily prepared by conventional chemical reactions. Various pyridinyl acylhydrazones of Formula I demonstrate broad-spectrum anthelmintic activity in sheep upon oral and/or parenteral administration.

2 Claims, No Drawings

ANTHELMINTIC PYRIDINYL ACYLHYDRAZONES

CROSS REFERENCE TO RELATED APPLICATIONS

This application is a continuation of Ser. No. 06/934,575, filed Oct. 3, 1986 (pending); which is the national phase of PCT/US86/00072 filed Jan. 23, 1986; which is a continuation-in-part of Ser. No. 715,425 filed Mar. 25, 1985 (now abandoned); which is a continuation-in-part of Ser. No. 700,375 filed Feb. 11, 1985 (now abandoned).

SUMMARY OF THE INVENTION

This invention pertains to a new method for killing and controlling worms (Helminths), and new formulations for killing and controlling worms in animals, and new chemical compounds. The invention is more particularly directed to a new method for killing and controlling parasitic worms in animals with certain pyridinyl acylhydrazones, to new anthelmintic formulations comprising the same, and to new pyridinyl acylhydrazones.

The anthelmintic pyridinyl acylhydrazones have the general structural formula I.

BACKGROUND OF THE INVENTION

The diseases or groups of diseases described generally as helminthiasis are due to infection of the animal with parasitic worms known as helminths. Helminthiasis and helminthosis are prevalent and may lead to serious economic problems in sheep, swine, cattle, goats, dogs, cats, horses, poultry and man. Among the helminths, the groups of worms known as nematodes, trematodes and cestodes cause widespread and oftentimes serious infections in various species of animals including man. The most common genera of nematodes and cestodes infecting the animals refered to above are Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Onchocerca, Taenia, Moniezia, Dipylidium, Metastrongylus, Macracanthorhynchus, Hyostrongylus, and Strongylus. Some of these genera attack primarily the intestinal tract while others, inhabit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

The anthelmintic activity of pyridinyl acylhydrazones has not been previously reported.

DETAILED DESCRIPTION OF THE INVENTION

The pyridinyl acylhydrazones of this invention, including hydrates or pharmaceutically acceptable salts thereof, are represented by Formula I wherein X is (a) hydrogen; (b) $C_1-C_{10}$ alkyl; (c) $C_2-C_6$ alkenyl, preferably $C_2-C_4$ alkenyl; (d) $C_2-C_6$ alkenyl; (e) cyclo($C_3-C_{10}$)alkyl optionally substituted with one, 2 or 3 $C_1-C_4$ alkyl, $C_2-C_4$ alkenyl, $C_1-C_4$ alkoxy, trifluoromethyl, or halo; (f) pyrrolidinyl; (g) piperidinyl; (h) 1-methylpyrrolidinyl; (i) 1-methylpiperidinyl; (j) $C_2-C_6$ alkoxyalkyl; (k) cyclo($C_3-C_{10}$)alkyl($C_1-C_4$)alkyl; (l) phenyl($C_1-C_4$)alkyl optionally substituted with one, 2 or 3 $C_1-C_4$ alkyl, $C_1-C_4$ alkoxy, halo, or trifluoromethyl; (m) phenoxy($C_1-C_4$)alkyl optionally substituted with one, 2 or 3 $C_1-C_4$ alkyl, $C_1-C_4$ alkoxy, halo, or trifluoromethyl; (n) naphthyl($C_1-C_3$)alkyl optionally substituted with one or two $C_1-C_4$ alkyl, $C_1-C_4$ alkoxy, halo or trifluoromethyl; (o) $C_1-C_6$ alkoxy, preferably $C_1-C_4$ alkoxy; (p) diphenylmethoxy; (q) cyclo($C_3-C_6$)alkyloxy optionally substituted with one or two $C_1-C_3$ alkyl; (r) phenoxy optionally substituted with one, 2 or 3 $C_1-C_4$ alkyl, $C_1-C_4$ alkoxy, halo, or trifluoromethyl; (s) benzyloxy optionally substituted with one, 2 or 3 $C_1-C_4$ alkyl, $C_1-C_4$ alkoxy, halo, or trifluoromethyl; with the proviso that when a 2-pyridinyl acylhydrazone and $R_1$, $R_2$, $R_4$ are hydrogen, $R_3$ is not benzyl; (t) heteroaromatic optionally substituted with one, 2 or 3 $C_1-C_4$ alkyl, $C_1-C_3$ alkoxy, halo, $C_1-C_3$ alkylthio, or trifluoromethyl; (u) phenyl optionally substituted with one, 2 or 3 $C_1-C_4$ alkyl, $C_1-C_3$ alkoxy, halo, trifluoromethyl, $C_2-C_6$ dialkylamino, $C_1-C_3$ alkylthio, nitro, or phenoxy optionally substituted with one, 2 or 3 $C_1-C_4$ alkyl, $C_1-C_3$ alkoxy, halo, or trifluoromethyl; (v) phenyl optionally substituted with the divalent $C_1-C_2$ alkylenedioxy; (w) naphthyl optionally substituted with one or 2 $C_1-C_4$ alkyl, $C_1-C_3$ alkoxy, halo, trifluoromethyl, $C_2-C_6$ dialkylamino, $C_1-C_3$ alkylthio, nitro; (x) bridged polycyclic hydrocarbon substituents of six to 10 nuclear carbons, optionally substituted with one, 2 or 3 ($C_1-C_3$) alkyl groups; (y) perhalo($C_1-C_7$)alkyl;

wherein $R_1$ and $R_2$, being the same or different, are hydrogen; hydroxy; $C_1-C_4$ alkyl, preferably $C_1-C_3$ alkyl; $C_1-C_3$ alkoxy; $C_1-C_3$ alkylthio; halo or trifluoromethyl;

wherein $R_3$ is hydrogen; $C_1-C_4$ alkyl; cyclo($C_3-C_6$)alkyl optionally substituted with one, 2 or 3 $C_1-C_3$ alkyl, preferably cyclo($C_3-C_5$)alkyl optionally substituted; phenyl optionally substituted with one, 2 or 3 $C_1-C_4$ alkyl, halo, trifluoromethyl, or $C_1-C_3$ alkoxy; phenyl($C_1-C_3$)alkyl optionally substituted with one, 2 or 3 $C_1-C_4$ alkyl, halo, trifluoromethyl, or $C_1-C_3$ alkoxy; or 1,3-dioxacyclohexan-5-yl;

wherein $R_4$ is hydrogen; $C_1-C_2$ alkyl; cyclo($C_3-C_6$)alkyl optionally substituted with one, 2 or 3 $C_1-C_3$ alkyl, preferably cyclo($C_3-C_5$)alkyl optionally substituted; phenyl optionally substituted with one, 2 or 3 $C_1-C_4$ alkyl, halo, trifluoromethyl, or $C_1-C_3$ alkoxy; phenyl($C_1-C_3$)alkyl optionally substituted with one, 2 or 3 $C_1-C_4$ alkyl, halo, trifluoromethyl, or $C_1-C_3$ alkoxy;

wherein n is zero or one.

$C_--C_-$ means the content of various hydrocarbon-containing moieties is indicated by a prefix designating the minimum and maximum number of carbon atoms in the moiety. Thus ($C_1-C_3$) alkyl refers to alkyl of one to 3 carbon atoms, inclusive or methyl, ethyl, propyl, and isopropyl.

Halogen atom (halo) refers to a bromo, chloro, iodo or fluoro atom.

Heteroaromatic refers to an aromatic heterocycle of 5 to 10 members, containing one or two heteroatoms selected from the group consisting of oxygen, nitrogen or sulfur and includes quinoline, pyrrole, indole, benzofuran, benzothiophene, quinazoline, quinoxaline, imidazole, pyrazole, oxazole, isoxazole, thiazole, isothiazole, pyridazine, pyrimidine, pyrazine, benzimidazole, benzothiazole, benzoxazole, pyridine, thiophene or furan, as well as the N-oxides, hydrates and pharmaceutically acceptable salts thereof.

Pharmaceutically acceptable refers to those properties and/or substances which are acceptable to the patient from a pharmacologically-toxicological point of view and to the manufacturing pharmacutical chemist from a physical-chemical point of view regarding composition, formulation, stability, patient acceptance and bioavailability.

Examples of $C_1$–$C_4$ alkyl are methyl, ethyl, propyl, butyl and isomeric forms thereof. Examples of $C_1$–$C_3$ alkoxy are methoxy, ethoxy, propoxy and isomeric forms thereof. Examples of phenoxy substituted with one, 2 or 3 $C_1$–$C_4$ alkyl are (o-, m-, or p-)tolyl, (o-, m-, or p-)ethylphenyl, p-tert-butylphenyl,2,5-dimethylphenyl,2,6-dimethylphenyl, 2,4-dimethylphenyl, (2,3,4-,2,3,5-,2,3,6-,2,4,6- or 2,4,5-)trimethylphenyl.

Examples of $C_2$–$C_6$ dialkylamino are dimethylamino, diethylamino, methylethylamino, dipropylamino and theylpropylamino.

Examples of phenyl($C_1$–$C_3$)alkyl are benzyl, phenylethyl and phenylpropyl. Examples of phenyl($C_1$–$C_3$)alkyl substituted with one, 2 or 3 $C_1$–$C_4$ alkoxy, halo or trifluoromethyl include 4-chlorobenzyl, 2-chlorophenylethyl, p-tolylethyl, 2-methylbenzyl, 4-methoxybenzyl. Examples of $C_1$–$C_3$ alkylthio include methylthio, ethylthio, and n-propylthio.

Examples of substituted cyclo($C_3$–$C_{10}$)alkyl are chrysanthemyl, 1-methylcyclopropyl and 2-methylcyclopropyl. Examples of cyclo($C_3$–$C_{10}$)alkyl($C_1$–$C_4$)alkyl are 2-cyclohexylethyl and cyclohexylmethyl. An example of substituted cyclo($C_3$–$C_6$)alkyloxy is menthyl.

Examples of naphthyl($C_1$–$C_3$)alkyl include 2-napthylmethyl and 1-naphthylethyl. Examples of substituted naphthyl($C_1$–$C_3$)alkyl is (3,8-dichloro-1-naphthyl)methyl; (4-chloro-1-naphthyl)methyl; and (4-methoxy-1-napthyl)methyl. Examples of substituted naphthyl include 3,6-dichloro-1-naphthyl; 3,5-dichloro-2-naphthyl; 6-methyl-2-naphthyl; and 4,6-dichloro-1-naphthyl.

Examples of bridged polycyclic hydrocarbon substituents of six to 10 nuclear carbons, optionally substituted with one, 2 or 3 ($C_1$–$C_3$) alkyl groups include exo or endo-2-norbonyl, bicyclo[2,2,2]oct-1-yl, and 1-adamantyl.

Examples of perhalo ($C_1$–$C_7$)alkyl include trifluoromethyl, n-heptafluoropropyl and n-undecafluoropentyl.

Prefered pyridinyl acylhydrazones of Formula I are 3-pyridinyl acylhydrazones or 4-pyridinyl acylhydrazones, most preferably are 4-pyridinyl acylhydrazones.

Preferred $R_1$ and $R_2$ include hydrogen, $C_1$–$C_3$ alkyl, $C_1$–$C_3$ alkoxy or a chloro atom.

Preferred $R_3$ includes hydrogen and methyl or ethyl. $R_4$ is preferably hydrogen.

Preferred X include hydrogen; $C_1$–$C_4$ alkyl; cyclohexylethyl; phenyl optionally substituted with one, 2 or 3 $C_1$–$C_2$ alkyl, $C_1$–$C_2$ alkoxy, trifluoromethyl and chloro; $C_1$–$C_4$ alkoxy; phenoxy optionally substituted with one, 2 or 3 $C_1$–$C_2$ alkyl, $C_1$–$C_2$ alkoxy, trifluoromethyl and chloro. Most preferably X includes hydrogen, $C_1$–$C_4$ alkyl; cyclohexylethyl; phenyl; phenyl substituted with $C_1$–$C_2$ alkoxy and ethoxy.

One embodiment of this invention includes, of course, the anthelmintic use and anthelmintic compositions of compounds of Formula I, IA, IB, IC, ID or IE, hydrates thereof or pharmaceutically acceptable salts thereof.

Still another embodiment of this invention are the novel compounds, hydrates thereof or pharmaceutically acceptable salts thereof according to Formula I.

Another embodiment of this invention are the compounds of Formula I, the hydrates thereof or pharmaceutically acceptable salts thereof where X is selected from (a) hydrogen; (b) $C_1$–$C_{10}$ alkyl; with the proviso that when X is methyl and the compound is a 2-pyridinyl acylhydrazone, and $R_1$, $R_2$ and $R_4$ are hydrogen, $R_3$ is other than hydrogen or methyl; with the further proviso that when X is methyl and the compound is a 4-pyridinyl acylhydrazone, and $R_1$, $R_2$ and $R_4$ are hydrogen, $R_3$ is other than hydrogen; (c) $C_2$–$C_6$ alkenyl; (d) $C_2$–$C_6$ alkynyl; (e) cyclo($C_3$–$C_6$)alkyl optionally substituted with one, 2 or 3 $C_1$–$C_4$ alkyl, $C_2$–$C_4$ alkenyl, $C_1$–$C_4$ alkoxy, trifluoromethyl, or halo; (j) $C_2$–$C_6$ alkoxyalkyl; (k) cyclo($C_4$–$C_{10}$)alkyl($C_1$–$C_4$)alkyl; (l) phenyl($C_1$–$C_3$)alkyl optionally substituted with one, 2 or 3 $C_1$–$C_4$ alkyl, $C_1$–$C_4$ alkoxy, halo, or trifluoromethyl; with the proviso that when X is phenylmethyl and $R_1$, $R_2$ and $R_4$ are hydrogen, $R_3$ is other than hydrogen or methyl; (m) phenoxy($C_1$–$C_4$)alkyl optionally substituted with $C_1$–$C_4$ alkyl, $C_1$–$C_4$ alkoxy, halo, or trifluoromethyl; with the proviso that when X is phenoxymethyl substituted with 4-chloro,2,4-dichloro or 2,4,5-trichloro and $R_1$, $R_2$ and $R_4$ are hydrogen, $R_3$ is other than hydrogen (n) naphthyl($C_1$–$C_3$)alkyl optionally substituted with one or 2 $C_1$–$C_4$ alkyl, $C_1$–$C_4$ alkoxy, halo, or trifluoromethyl; with the proviso that when X is 1-naphthylmethyl and $R_1$, $R_2$ and $R_4$ are hydrogen, $R_3$ is other than hydrogen or methyl; (o) $C_1$–$C_6$ alkoxy; with the proviso that when the compound is a 4-pyridinyl acylhydrazone and $R_1$, $R_2$, $R_3$ and $R_4$ are hydrogen, X is other than methoxy; with the further proviso that when the compound is a 3-pyridinyl acylhydrazone and $R_1$, $R_2$ and $R_4$ are hydrogen and $R_3$ is methyl, X is other than ethoxy; with the further proviso that when the compound is a 2-pyridinyl acylhydrazone and $R_1$, $R_2$ and $R_4$ are hydrogen, X is other than methoxy when $R_3$ is methyl, or ethoxy when $R_3$ is hydrogen or methyl; (p) diphenylmethoxy; (q) cyclo($C_3$–$C_6$)alkyloxy optionally substituted with one or two $C_1$–$C_3$ alkyl; (r) phenoxy optionally substituted with one, 2 or 3 $C_1$–$C_4$ alkyl, $C_1$–$C_4$ alkoxy, halo, or trifluoromethyl; (s) benzyloxy optionally substituted with one, 2 or 3 $C_1$–$C_4$ alkyl, $C_1$–$C_4$ alkoxy, halo, or trifluoromethyl; with the proviso that when a 2-pyridinyl aclhydrazone and $R_1$, $R_2$, $R_4$ are hydrogen, $R_3$ is not benzyl; (u) phenyl optionally substituted with one, 2 or 3 $C_1$–$C_4$ alkyl, $C_1$–$C_3$ alkoxy, halo, trifluoromethyl, $C_2$–$C_6$ dialkylamino, $C_1$–$C_3$ alkylthio, nitro, or phenoxy optionally substituted with one, 2 or 3 $C_1$–$C_4$ alkyl, $C_1$–$C_3$ alkoxy, halo, or trifluoromethyl; with the proviso that when X is phenyl and $R_1$ and $R_2$ are hydrogen, either $R_3$ or $R_4$ is other than hydrogen; with the further proviso that when X is phenyl and the compound is a 2- or 4-pyridinyl acylhydrazone and $R_1$, $R_2$ and $R_4$ are hydrogen, $R_3$ is other than hydrogen; with the further proviso that when X is phenyl, $R_1$ is 2-ethyl, $R_2$, $R_3$ and $R_4$ are hydrogen, the compound is other than a 4-pyridinyl acylhydrazone; with the further proviso that when X is phenyl substituted with 4-dimethylamino and $R_1$, $R_2$, $R_3$ and $R_4$ are hydrogen, the compound is other than a 4-pyridinyl acylhydrazone; with the further proviso that when X is phenyl substituted with 4-methyl, the compound is a 2- or 4-pyridinyl acylhydrazone, either $R_1$, $R_2$, $R_3$ or $R_4$ is other than hydrogen; with the further proviso that when X is phenyl substituted with 4-methoxy, $R_3$ is methyl, and $R_1$, $R_2$ and $R_4$ are hydrogen, the compound is other than a 4-pyridinyl achlhydrazone; with the further proviso that when X is phenyl substituted with 3,4-dimethoxy, $R_1$ is 2-ethyl and $R_2$, $R_3$ and $R_4$ are hydrogen, the compound is other than a 4-pyridinyl acylhydrazone; with the further proviso that when X is phenyl substituted with 4-t-butyl and $R_1$, $R_2$, $R_3$ and $R_4$ are hydrogen, the compound is other than a 3-pyridinyl acylhydrazone; with the further proviso that when X is phenyl, $R_1$, $R_2$ and $R_4$ are hydrogen, and $R_3$ is benzyl, the compound is other than a 2-pyridinyl acylhydrazone; with the further proviso that when X is phenyl substituted with 2-nitro, either $R_2$, $R_3$ or $R_4$ is other than hydrogen; with the further proviso that when X is phenyl substituted with 4-nitro, $R_1$ is 2-ethyl, and $R_2$, $R_3$ and $R_4$ are hydrogen, the compound is other than a 4-pyridinyl acylhydrazone; with the further proviso that when X is phenyl substituted with 4-nitro, $R_3$ is methyl, and $R_1$, $R_2$ and $R_4$ are hydrogen, the compound is other than a 4-pyridinyl acylhydrazone; (v) phenyl optionally substituted with the divalent $C_1$-$C_2$ alkylenedioxy; and (w) naphthyl optionally substituted with one or 2 $C_1$-$C_4$ alkyl, $C_1$-$C_3$ alkoxy, halo, trifluoromethyl, $C_2$-$C_6$ dialkylamino, $C_1$-$C_3$ alkylthio, nitro;

Another embodiment of this invention are the compounds of IB and the novel compounds of Formula IA, IC, ID or IE; the hydrates thereof or pharmaceutically acceptable salts thereof.

Another embodiment of this invention are the novel compounds of Formula IA, the hydrates thereof or pharmaceutically acceptable salts thereof where $R_5$, $R_6$ and $R_7$ are the same or diferent and are selected from the group consisting of hydrogen, $C_1$-$C_4$ alkyl, $C_1$-$C_3$ alkoxy, trifluoromethyl, a halogen atom, $C_1$-$C_4$ alkylthio, phenoxy optionally substituted with a halogen atom, trifluoromethyl, $C_1$-$C_4$ alkyl, $C_1$-$C_3$ alkoxy; with the proviso that at least either $R_5$, $R_6$ or $R_7$ is other than hydrogen.

Preferred $R_5$, $R_6$ and $R_7$ include hydrogen, methyl, ethyl, methoxy, ethoxy, trifluoromethyl and chloro.

Another embodiment of this invention are the novel compounds of Formula IB, the hydrates thereof or pharmaceutically acceptable salts thereof where $R_8$ and $R_9$ are the same or different and are selected from the group consisting of hydrogen, $C_1$-$C_4$ alkyl, $C_1$-$C_3$ alkoxy, trifluoromethyl, a halogen atom, $C_1$-$C_4$ alkylthio, $C_2$-$C_6$ dialkylamino and nitro.

Preferred $R_8$ and $R_9$ include hydrogen, methyl, ethyl, methoxy, ethoxy, trifluoromethyl and chloro.

Another embodiment of this invention are the novel compounds of Formula IC, the hydrates thereof or pharmaceutically acceptable' salts thereof where —$OR'_5$ is selected from the group consisting of (o) $C_1$-$C_6$ alkoxy, preferably $C_1$-$C_4$ alkoxy; (p) diphenylmethoxy; (q) cyclo($C_3$-$C_6$)alkyloxy optionally substituted with one or two $C_1$-$C_3$ alkyl; (r) phenoxy optionally substituted with one, 2 or 3 $C_1$-$C_4$ alkyl, $C_1$-$C_4$ alkoxy, halo, or trifluoromethyl; or (s) benzyloxy optionally substituted with one, 2 or 3 $C_1$-$C_4$ alkyl, $C_1$-$C_4$ alkoxy, halo, or trifluoromethyl.

Another embodiment of this invention are the compounds of Formula IC, the hydrates thereof or pharmaceutically acceptable salts thereof where —$OR'_5$ is selected from the group consisting of (o) $C_1$-$C_6$ alkoxy, preferably $C_1$-$C_4$ alkoxy; (p) diphenylmethoxy; (q) cyclo($C_3$-$C_6$)alkyloxy optionally substituted with one or two $C_1$-$C_3$ alkyl; (r) phenoxy optionally substituted with one, 2 or 3 $C_1$-$C_4$ alkyl, $C_1$-$C_4$ alkoxy, halo, or trifluoromethyl; or (s) benzyloxy optionally substituted with one, 2 or 3 $C_1$-$C_4$ alkyl, $C_1$-$C_4$ alkoxy, halo, or trifluoromethyl; with the proviso that when a 4-pyridinyl acylhydrazone and $R_1$, $R_2$, $R_3$ and $R_4$ are hydrogen, —$OR'_5$ is other than methoxy; with the further proviso that when a 3-pyridinyl acylhydrazone and $R_1$, $R_2$ and $R_4$ are hydrogen and $R_3$ is methyl, —$OR'_5$ is other than ethoxy; with the further proviso that when a 2-pyridinyl acylhydrazone and $R_1$, $R_2$ and $R_4$ are hydrogen, —$OR'_5$ is other than (a) methoxy when $R_3$ is methyl, or (b) ethoxy when $R_3$ is hydrogen or methyl.

Another embodiment of this invention are the novel compounds of Formula ID, the hydrates thereof or pharmaceutically acceptable salts thereof where —$R''_5$ is selected from the group consisting of (a) hydrogen; (b) $C_1$-$C_{10}$ alkyl; (c) $C_2$-$C_6$ alkenyl, preferably $C_2$-$C_4$ alkoxy; (d) $C_2$-$C_6$ alkynyl; (e) cyclo($C_3$-$C_6$)alkyl optionally substituted with one, 2 or 3 $C_1$-$C_4$ alkyl, $C_2$-$C_4$ alkenyl, $C_1$-$C_4$ alkoxy, trigluoromethyl, or halo; (f) pyrrolidinyl; (g) piperidinyl; (h) 1-methylpyrrolidinyl; (i) 1-methylpiperidinyl; (j) $C_2$-$C_6$ alkoxyalkyl; (k) cyclo($C_4$-$C_{10}$)alkyl($C_1$-$C_4$)alkyl; (l) phenyl($C_1$-$C_3$)alkyl optionally substituted with one, 2 or 3 $C_1$-$C_4$ alkyl, $C_1$-$C_4$ alkoxy, halo, or trifluoromethyl; (m) phenoxy($C_1$-$C_4$)alkyl optionally substituted with $C_1$-$C_4$ alkyl, $C_1$-$C_4$ alkoxy, halo, or trifluoromethyl; or (n) naphthyl($C_1$-$C_3$)alkyl optionally substituted with one or 2 $C_1$-$C_4$ alkyl, $C_1$-$C_4$ alkoxy, halo, or trifluoromethyl.

$R_1$, $R_2$, $R_3$, $R_4$ and n are defined in Formulas IA, IB, IC, ID, and IE as in Formula I.

Among the pyridinyl acylhydrazones of Formula IA:

benzoic acid (3-pyridinylmethylene)hydrazide (Cpd #6), benzoic acid (4-pyridinylmethylene)hydrazide (Cpd #7), benzoic acid [1-(2-pyridinyl)ethylidene]hydrazide (Cpd #1), benzoic acid (2-pyridinylmethylene)hydrazide (Cpd #9, hydrate), 4-dimethylaminobenzoic acid (4-pyridinylmethylene)hydrazide, 4-methylbenzoic acid (2-pyridinylmethylene)hydrazide (Cpd #4, hydrate), 4-methylbenzoic acid (4-pyridinylmethylene)hydrazide (Cpd #33), 4-methylbenzoic acid (2-pyridinylmethylene)hydrazide 1-oxide, 4-t-butylbenzoic acid (3-pyridinylmethylene)hydrazine, 2-nitrobenzoic acid (4-pyridinylmethylene)hydrazide (Cpd #69), 2-nitrobenzoic acid (2-pyridinylmethylene)hydrazide, 2-nitrobenzoic acid (3-pyridinylmethylene)hydrazide, 4-nitrobenzoic acid [(2-ethyl-4-pyridinyl)methylene]hydrazide, benzoic acid [(2-ethyl-4-pyridinyl)methylene]hydrazide, 3,4-dimethoxybenzoic acid [2-(ethyl-4-pyridinyl)methylene]hydrazide, benzoic acid [1-(4-pyridinyl)ethylidene]hydrazide (Cpd #3), 4-methoxybenzoic acid [1-(4-pyridinyl)ethylidene]hydrazide, 4-nitrobenzoic acid [1-(4-pyridinyl)ethylidene]hydrazide, and benzoic acid (α-2-pyridinylbenzylidene)hydrazide are known. See Y. Nishimoto and S. Toyashimo, Yakuguku Zasshi 87, 27-32, (1967); Chem. Abst. 66, 98544r; S. E. Livingstone and J. E. Oluka, Transition Met. Chem 3, 261-7 (1978); H. Schlesinger, U.S. Pat. No. 3,066,023, 11/27/62 - cf. H. Schlesinger, Ger. Patent 1,101,145, Appl 12/19/58-Chem Abst. 56, P2104b; S. Tanaka, T. Kato, S. Yamamoto and H. Yoshiaka, Agric. Biol. Chem. 41, 1953-1959 (1977); A. C. Sartorelli, K. C. Agrawal, B. A. Booth, J. Pittman, D. G. Bartholomew and A. D. Bloom, J. Med. Chem. 19, 830-833 (1976); A. Pedrazzoli et al., Bull. Soc. Chim. Fr., 407-14 (1968), Chem. Abst. 69, 27401T; I. Babic et al., Chim. Ther. 7, 220-2 (1972); Y. Arata et al, Am. Rept. Fac. Pharm. Kanazawa Univ., No. 5, 46-9 (1955), Chem. Abst. 50, 14974e; Chem. Abst. 101, 1624ot.

Among the pyridinyl acylhydrazones of Formula IC; ethyl[1-(3-pyridinyl)ethylidene]carbazate (Cpd #71), methyl (2-pyridinylmethylene)carbazate, ethyl(2-pyridinylmethylene)carbazate (Cpd #73), ethyl(4-pyridinylmethylene)carbazate (Cpd #75), and ethyl [1-(2-pyridinyl)ethylidene]carbazate (Cpd #70). are known. See R. U. Lemieux and R. Raap, U.S. Pat. No. 3,654,294, 04/04/72; Chem Abst. 77, 5448b; J. Amat Badrinas, Spain Patent, ES 490,004 A1, 04/01/81; Chem. Abstr. 96, 34898w; N. R. El-Rayyer and F. M. Al-Kharafi, Egypt. J. Chem. 23, 151-6 (1981); Chem. Abst. 96, 14575x; N. R. ElRayyes and A. H. Katric, J. Chem. Eng. Data 28, 132-4 (1983); and A. B. deMilo, R. E. Redfern and A. B. Borkovec, J. Agri. Food Chem. 31, 713-18 (1983).

Amont the pyridinyl acylhydrazones of Formula ID;
acetic acid (4-pyridinylmethylene)hydrazide,
acetic acid (2-pyridinylmethylene)hydrazide,
acetic acid [1-(2-pyridinyl)ethylidene]hydrazide,
2,4,5-trichlorophenoxyacetic acid (4-pyridinylmethylene)hydrazide,
2,4,5-trichlorophenoxyacetic acid (3-pyridinylmethylene)hydrazide,
2,4,5-trichlorophenoxyacetic acid (2-pyridinylmethylene)hydrazide,
2,4,-dichlorophenoxyacetic acid (4-pyridinylmethylene)hydrazide,
2,4-dichlorophenoxyacetic acid (3-pyridinylmethylene)hydrazide,
2,4-dichlorophenoxyacetic acid (2-pyridinylmethylene)hydrazide,
4-chlorophenoxyacetic acid (4-pyridinylmethylene)hydrazide,
4-chlorophenoxyacetic acid (3-pyridinylmethylene)hydrazide,
4-chlorophenoxyacetic acid (2-pyridinylmethylene)hydrazide,
1-napthylacetic acid [1-(3-pyridinyl)ethylidene]hydrazide,
1-napthylacetic acid [1-(4-pyridinyl)ethylidene]hydrazide,
1-napthylacetic acid [1-(2-pyridinyl)ethylidene]hydrazide,
1-napthylacetic acid (2-pyridinylmethylene)hydrazide,
1-napthylacetic acid (3-pyridinylmethylene)hydrazide,
1-napthylacetic acid (4-pyridinylmethylene)hydrazide,
phenylacetic acid [1-(2-pyridinyl)ethylidene]hydrazide,
phenylacetic acid [1-(3-pyridinyl)ethylidend]hydrazide,
phenylacetic acid [1-(4-pyridinyl)ethylidene]hydrazide (Cpd #157),
phenylacetic acid (2-pyridinylmethylene)hydrazide,
phenylacetic acid (3-pyridinylmethylene)hydrazide, and
phenylacetic acid (4-pyridinylmethylene)hydrazide
are known. See G. Palla, C. Pelizzi, G. Prediери and C. Vignalo, Grazz. Chim. Ital. 112 (7-8), 339-41 (1982) - Chem. Abstr. 98, (13), 106703v; C. Mochon and G. Azira, Microchem. Journal, 1981, 26 (4), 463-71 - Chem. Abstr. 96 (8), 62225t; S. E. Livingstone and J. E. Oluka, Trans. Met. Chem. 3, 261-7 (1978); J. Klosa, J. Prakt. Chem., 31 (1-2), 20-33 (1966) - Chem. Abstr. 64, 11124a; N. B. Mahishi, B. H. Iyer and M. Sirisi, J. Indian Chem. Soc., 42 (2), 67-74 (1965) - Chem. Abstr. 62, 16654g; H. Bojarska-Dahlig, Acta Polon Pharm., 20 (4), 293-302 (1963) - Chem. Abstr. 62, 2975i; N. R. El-Rayyes and F. M. Al-Kharafi, Egypt. J. Chem., 23, 151-6 (1981) - Chem. Abstr., 96, 142575x; H. Bojarska-Dahlig, Acta Polon. Pharm., 21 (4), 337-41 (1967) - Chem. Abstr. 62, 104016; Y. Takeda, Y. Maejima and H. Namekata, Japan J. Tuberc. 2, 184-5 (1954), Chem. Abstr. 49, 13243i.

Among the pyridinyl acylhydrazones of Formula IE:
isonicotinic acid (2-pyridinylmethylene)hydrazide (Cpd #221),
isonicotinic acid [1-(4-pyridinyl)ethylidene]hydrazide (Cpd #217),
picolinic acid (2-pyridinylmethylene)hydrazide,
picolinic acid [1-(4-pyridinyl)ethylidene]hydrazide,
picolinic acid [(6-methyl-2-pyridinyl)methylene]hydrazide,
quinaldic acid [(6-methyl-2-pyridinyl)methylene]hydrazide,
4,5-dimethyl-2-furancarboxylic acid (4-pyridinylmethylene)hydrazide,
4,5-dimethyl-2-furancarboxylic acid (3-pyridinylmethylene)hydrazide,
4,5-dimethyl-2-furancarboxylic acid (2-pyridinylmethylene)hydrazide,
5-ethyl-2-furancarboxylic acid (4-pyridinylmethylene)hydrazide,
5-ethyl-2-furancarboxylic acid (3-pyridinylmethylene)hydrazide,
5-ethyl-2-furancarboxylic acid (2-pyridinylmethylene)hydrazide,
5-methyl-2-furancarboxylic acid (4-pyridinylmethylene)hydrazide,
5-methyl-2-furancarboxylic acid (3-pyridinylmethylene)hydrazide,
5-methyl-2-furancarboxylic acid (2-pyridinylmethylene)hydrazide,
nicotinic acid (3-pyridinylmethylene)hydrazide,
indole-3-carboxylic acid (4-pyridinylmethylene)hydrazide,
indole-2-carboxylic acid (4-pyridinylmethylene)hydrazide,
indole-2-carboxylic acid (3-pyridinylmethylene)hydrazide,
indole-2-carboxylic acid (2-pyridinylmethylene)hydrazide,
isonicotinic acid (3-pyridinylmethylene)hydrazide,
nicotinic acid (2-pyridinylmethylene)hydrazide,
nicotinic acid (4-pyridinylmethylene)hydrazide,
picolinic acid (2-pyridinylmethylene)hydrazide,
picolinic acid (3-pyridinylmethylene)hydrazide,
picolinic acid (4-pyridinylmethylene)hydrazide,
isonicotinic acid (4-pyridinylmethylene)hydrazide (Cpd #220),
pyrazine-2-carboxylic acid [(2-ethyl-4-pyridinyl)methylene]hydrazide,
nicotinic acid [(2-ethyl-4-pyridinyl)methylene]hydrazide,
isonicotinic acid [(2-ethyl-4-pyridinyl)methylene]hydrazide, 2-ethylpyridine-4-carboxylic acid [(2-ethyl-4-pyridinyl)methylene]hydrazide,
4,5-dichloroquinolinic-2-carboxylic acid (4-pyridinylmethylene)hydrazide,
4,5-dichloroquinoliine-2-carboxylic acid (3-pyridinylmethylene)hydrazide,
6-methyl-3-pyridinecarboxylic acid [1-(6-methyl-3-pyridinyl)ethylidene]hydrazide,
3-n-propyl-1,4-dioxoquinoxaline-2-carboxylic acid (2-pyridinylmethylene)hydrazide,
3-methyl-1,4-dioxoquinoxaline-2-carboxylic acid (2-pyridinylmethylene)hydrazide,
3-ethyl-1,4-dioxoquinoxaline-2-carboxylic acid (2-pyridinylmethylene)hydrazide,
4-methyl-2-pyridinecarboxylic acid (α-2-pyridinylbenzylidene)hydrazide,
picolinic acid (α-2-pyridinylbenzylidene)hydrazide,
5-n-butyl-2-pyridinecarboxylic acid (4-pyridinylmethylene)hydrazide,
5-n-butyl-2-pyridinecarboxylic acid (3-pyridinylmethylene)hydrazide,
5-n-butyl-2-pyridinecarboxylic acid (2-pyridinylmethylene)hydrazide,
isonicotinic acid N-oxide [1-(4-pyridinyl)ethylidene]hydrazide,
isonicotinic acid [1-(4-pyridinyl)ethylidene]hydrazide 1-oxide,
isonicotinic acid N-oxide [1-(4-pyridinyl)ethylidene]hydrazide 1-oxide,
isonicotinic acid [1-(6-methyl-2-pyridinyl)ethylidene]hydrazide,
isonicotinic acid [1-(2-pyridinyl)ethylidene]hydrazide (Cpd #219),
nicotinic acid [1-(2-pyridinyl)ethylidene]hydrazide (Cpd #200),
nicotinic acid [1-(6-methyl-2-pyridinyl)ethylidene]hydrazide,
isonicotinic acid [1-(2-pyridinyl)ethylidene]hydrazide (Cpd #218),
nicotinic acid [1-(3-pyridinyl)ethylidene]hydrazide (Cpd #199),
isonicotinic acid (α-2-pyridinylbenzylidene)hydrazide,
thiophene-2-carboxylic acid [1-(2-pyridinyl)ethylidene]hydrazide,
furan-2-carboxylic acid (2-pyridinylmethylene)hydrazide (Cpd #216, hydrate),
quinaldic acid (2-pyridinylmethylene)hydrazide,
5-n-butyl-2-pyridine carboxylic acid [1-methyl-3-pyridinium]hydrazide methanesulfonate,
indazole-3-carboxylic acid (4-pyridinylmethylene)hydrazide;
isonicotinic acid [(3-hydroxy-4-pyridinyl)methylene]hydrazide; and
pyridazine carboxylic acid (4-pyridinylmethelene)hydrazide are known. See M. Nonoyama, Inorg. Chim. Acta. 10, 133-137 (1974); A. L. Mndzhoyan, V. G. Afrikyan, R. S. Organesyan, A. O. Shakhmuradova, L. D. Zhuruli, S. G. Karagezan and V. G. Sarafyar, Arm. Khim. Zh. 21, 340-7 (1968); D. Koruncev, S. Cvetnic and I. Babic, Acta. Pharm. Jugoslav, 23, 1-8 (1973); D. Koruncev, I. Babic, D. Cvek and A. Deljac, Acta. Pharm. Jugoslav, 24, 9-11 (1974); M. Kawai, U.S. Pat. No. 3,503,987, Jan. 17, 1970. Chem. Abstr., 72, 121378z; W. Durckheimer, H. Hartung and E. Schrinner, Ger. Offen. DE 2002712, Jul. 29, 1971; Chem. Abstr. 75, 98595a; F. Capitan, F. Salinas and J. Giminez Plaza, Afinidad, 35, 263-5 (1978); F. H. Case, J. Heterocycl. Chem., 10, 353-5 (1973); H. Vogt and H. Mayer, Arzneim. Forsch., 20, 1532-6 (1970); A. Risaliti and L. Lolli, Farmaco (Pavic) Ed. Sci., 12, 705-11 (1957), Chem. Abstr., 52, 11038f; N. P. Buu-Hoi and N. Dut Xaong., Bull. Soc. Chim. France, 1377-9 (1961); M. L. Vitalo, J. Webb and P. Saltman, J. Inorg. Biochem., 20, 255-62 (1984); A. Alemany, M. Bernabe, C. Eloriagu, E. F. Alvarez, M. Lora-Tamajo and J. Ofelia Nieto, Bull. Soc. Chim. France, 2486-2497 (1966); F. Capitan, F. Salinar and J. Giminez Plaza, Ars. Pharm., 16, 293-304 (1975); Chem. Abstr., 84, 11787x; S. E. Livingstone and J. E. Oluka, Trans. Met. Chem., 3, 261-7 (1978); E. Requena, J. J. Laserna, A. Novar, and F. G. Sanchez, Analyst, 108, 933-38 (1983); E. Baker et al, Biochemical Pharmacology, 37, 3011-3017 (1985); H. Bojarska-Dahlig, Rec. Trav. Chim. 83, pp. 177-85 (1964), Chem. Abstr., 60, 14467d.

The preparation of piperonylic acid (4-pyridinylmethylene)hydrazide (Cpd #19) and 3,4,5-trimethoxybenzoic acid (4-pyridinylmethylene)hydrazide (Cpd #224) is described in G. Mazzone et al, J. Heterocyclic Chem., 21, 181 (Jan.-Feb. 1984).

The pyridinyl acylhydrazones of this invention (Formula I) are readily prepared by reacting the appropriate pyridyl ketone (II) with the acylhydrazide/carbazate (III) (Chart A, Scheme A) or by heating the pyridyl ketone (II) with the appropriate hydrazine (IV) to form the hydrazone intermediate (V) which is then acylated with the halide or anhydride (VI) to form the pyridinyl acylhydrazone (I) (Chart A, Scheme B).

The pyridinyl acylhydrazone N-oxides (formula I where n=1) are generally prepared by first oxidizing the pyridylketone (II) to furnish the pyridylketone N-oxide (VII) (Scheme C). The ketone VII is then reacted with the appropriate acylhydrazide or carbazate (III) to give the pyridinyl acylhydrazone N-oxide (I) or alternatively the pyridinylacylhydrazone (I) is formed by first reacting the ketone VII with a hydrazine IV to form hydrazone intermediate N-oxide VIII which is in the final step is acylated with the halide VI to furnish the pyridinyl acylhydrazone N-oxide I.

The reaction of Scheme A is carried out in the presence of a suitable solvent, for example, water, alcohols, ethers, halogenated hydrocarbons, hydrocarbons and include methanol, ethanol, isopropanol, propanol, hexane, tetrahydrofuran, dioxane, methylene chloride, preferably ethanol. A catalyst such as glacial acetic acid, hydrochloric acid, sulfuric acid or p-toluenesulfonic acid can be utilized to enhance the yield/rate of the reaction, particularly when $R_3$ is alkyl of 3 or more atoms, arylalkyl or aryl.

The acylation reaction of Scheme B is carried out in the presence of a suitable base such as a tertiary amine, for example, triethylamine or preferably, pyridine. The base may also be the solvent.

The desired N-oxide is prepared by oxidizing the appropriate ketone using a peracid such as perbenzoic, m-chlorobenzoic, performic peracetic or generating the peracid in situ preferably with hydrogen peroxide/acetic acid to furnish the pyridinyl ketone N-oxide which is reacted with the appropriate hydrazide or carbazate (Chart A, Scheme C).

The starting compounds are known or can be readily prepared by known methods. R. L. Frank and C. Weatherbee, J. Am. Chem. Soc., 70, 3482-3 (1948); N. B. Mahishi, et al., J. Indian Chem. Soc., 42 67-74 (1965) and M. Ogata and H. Kano, Chem. Pharm. Bull (Tokyo), 11, 32 (1963).

The following detailed examples/procedures describe how to prepare various pyridinyl acylhydrazones of the invention and are to be construed as merely illustrative, and not limitations of the preceding disclosure in any way whatsoever. Those skilled in the art will promptly recognize appropriate variations from the procedures both as to reactants as well as to reaction conditions and techniques.

Procedure 1

Preparation of benzoic acid [1-(2-pyridinyl)ethylidene]hydrazide, Compound 1

A mixture of 6.81 gm (0.05 mole) of benzhydrazide, 6.06 gm (0.05 mole) of 2-acetylpyridine and 100 ml of ethanol is stirred at reflux 2 hr. Then sufficient dioxane is added to the boiling mixture to furnish a solution. The hot solution is filtered. The filtrate is diluted to the cloud point with water, cooled to room temperature, and then chilled in the refrigerator. The product is collected and dried to yield 7.61 gm (64%) of the title compound having a melting point of 151.6° C.

Analysis Calcd: C, 70.29; H, 5.44
Found: C, 70.28; H, 5.43.

Procedure 2

Preparation of 2-methylbenzoic acid [1-(4-pyridinyl)ethylidene]hydrazide, Compound 10

A mixture of 3.63 gm (0.03 mole) of 4-acetylpyridine, 4.51 gm (0.03 mole) of o-toluic acid hydrazide and 100 ml of 95% ethanol is refluxed 8 hr. The hot solution is filtered. The filtrate is diluted with water to the cloud point and cooled to room temperature. The mixture is chilled in the refrigerator and the product collected, washed with water, and dried to yield 4.78 gm (63%) of the title compound having a melting point of 187.4° C.

Analysis Calcd: C, 71.15; H, 5.93; N, 16.60.
Found: C, 70.82; H, 5.86; N, 16.61

Procedure 3

Preparation of benzoic acid [1-(4-pyridinyl)ethylidene]hydrazide 1-oxide, Compound 48

A mixture of 5.48 gm (0.04 mole) of 4-acetylpyridine 1-oxide, 5.45 gm (0.04) of benzhydrazide and 100 ml of absolute ethanol is refluxed for a total of 4 hr and cooled. The reaction mixture is evaporated in vacuo to yield a solid which is crystallized from ethanol to yield 7.82 gm (77%) of the title compound having a melting point of 248.9° C. (decomp).

Analysis Calcd: C, 65.88; H, 5.10; N, 16.47.
Found: C, 65.44; H, 5.23; N, 16.39.

Procedure 4

Preparation of benzoic acid [1-(4-pyridinyl)propylidene]hydrazide, Compound 51

A mixture of 4.05 gm (0.03 mole) of 4-propionylpyridine, 4.08 gm (0.03 mole) of benzyhydrazide and 100 ml of Ethanol is refluxed 6 hr. The hot solution is filtered. The filtrate is cooled to room temperature and then chilled in the refrigerator. The product is colected, washed with Skellysolve B and dried to yield 5.36 gm (71%) of the title compound having a melting point of 177.6° C.

Analysis Calcd: C, 71.15; H, 5.93; N, 16.60.
Found: C, 71.13 H, 5.98; N, 16.77.

Procedure 5

Preparation of 2-phenoxybenzoic acid [3-methyl-1-(4-pyridinyl)butylidene]hydrazide, Compound 54

Following the general method of procedure 4 and making noncritical variations, except 12 drops of glacial acetic acid is added as a catalyst, 9.00 gm (0.055 mole) of isobutyl 4-pyridyl ketone and 12.59 gm (0.055 mole) of 2-phenoxybenzhydrazide yield 13.89 gm (67%) of the title compound having a melting point of 137.6° C.

Analysis Calcd: C, 73.97; H, 6.21; N, 11.25.
Found: C, 74.16; H, 6.24; N, 11.19.

Procedure 6

Preparation of benzoic acid 1-methyl-2-[1(4-pyridinyl)ethylidene]hydrazide, Compound 55

To 100 ml of pyridine is added successively, under dry nitrogen, 8.83 gm (0.0592 mole) of 1-methyl-2-[1-(4-pyridinyl)ethylidene]hydrazine and 6.87 gm (0.0592 mole) of benzoyl chloride. Upon addition of the acid chloride the color changes from clear orange to a clear, deep rose color which changes to an orange solid within about 5 minutes. The reaction mixture is stirred at room temperature overnight, the pyridine removed via a Buchi evaporator at 70° C. and the cooled residue slurried with water to yield 6.32 gm (42%) of the title compound having a melting point of 128.3° C.

Analysis Calcd: C, 71.13; H, 5.97; N, 16.59.
Found: C, 71.02; H, 6.02; N, 16.27.

Procedure 7

Preparation of benzoic acid [1-(3-pyridinyl)propylidene]hydrazide, Compound 58

A mixture of 6.76 gm (0.05 mole) of 3-propionylpyridine, 6.81 gm (0.05 mole) of benzhydrazide and 100 ml of absolute ethanol is refluxed 8.5 hr. The hot solution is filtered. The filtrate is cooled to room temperature and then chilled. The crystals that separate are collected and dried to yield 10.18 gm (80%) of the title compound having a melting point of 169.4° C.

Analysis Calcd: C, 71.15; H, 5.93; N, 16.60
Found: C, 71.46; H, 5.97; N, 16.52.

Procedure 8

Preparation of benzoic acid [1-(4-pyridinyl)pentylidene]hydrazide, Compound 60

A mixture of 5.97 gm (0.0366 mole) of n-butyl 4-pyridinyl ketone, 5.45 gm (0.04 mole) of benzoic acid hydrazide and 100 ml of absolute ethanol is refluxed 4.5 hr. The hot solution is filtered. The filtrate is diluted with water to the cloud point, cooled to room temperature and chilled. The solids which deposit are collected, washed with water and dried to yield 7.89 gm (77%) of the title compound having a melting point of 142.1° C.

Analysis Calcd: C, 72.60; H, 6.76; N, 14.95.
Found: C, 72.83; H, 6.86; N, 14.90.

Procedure 9

Preparation of 2-methoxybenzoic acid [3-methyl-1-(4pyridinyl)butylidene]hydrazide, Compound 65

To 9.00 gm (0.0551 mole) of isobutyl 4-pyridyl ketone in 100 ml of absolute ethanol is added 9.20 gm (0.0551 mole) of 2-methoxybenzhydrazide and 12 drops of glacial acetic acid. The reaction mixture is refluxed on the steam bath overnight, filtered hot, the volume reduced to ½, titrated with cold water to the cloud point and set aside. Crystals do not form at room temperature nor in the freezer. The product is extracted in chloroform, the extracts washed 2x with water, dried with saturated sodium chloride solution and anhydrous sodium sulfate and the solvent removed via a rotoevaporator at 70° C. until a solid forms (2 hours); mp. 130.4° C.

Analysis Calcd: C, 69.43; H, 6.80; N, 13.49.
Found: C, 69.03; H, 6.72; N, 13.30.

Procedure 10

Preparation of benzoic acid [2-phenyl-1-(4-pyridinyl)ethylidene]hydrazide, Compound 61

Following the general method of procedure 9 and making non-critical variations, except 12 drops of glacial acetic acid was used, 6.00 gm (0.0304 mole) of benzyl 4-pyridyl ketone and 4.14 gm (0.0304 mole) of benzhydrazide yield 8.90 gm (93%) of the title compound in two crops melting at 84.4° and 90.0°.

Analysis Calcd: C, 76.17; H, 5,43; N, 13.32.
Found: C, 75.15; H, 5.45; N, 13.19.
C. 74.88; H, 5.42; N, 13.03.

Procedure 11

Preparation of ethyl [1-(2-pyridinyl)ethylidene]carbazate, Compound 70

A mixture of 6.06 gm (0.05 mole) of 2-acetylpyridine, 5.21 gm (0.05 mole) of ethylcarbazate and 100 ml of absolute ethanol is refluxed 2 hr. The hot solution is filtered. The filtrate is cooled to room temperature and then chilled in the refrigerator. The product is collected, washed with Skellysolve B and dried to yield 3.8 gm (37%) of the title compound having a melting point of 113.2° C.

Analysis Calcd: C, 59.97; H, 6.28; N, 20.29.
Found: C, 58.05; H, 6.33; N, 20.64.

Procedure 12

Preparation of benzyl (α-2-pyridinylphenethylidene)carbazate, Compound 77

A mixture of 8.31 gm (0.05 mole) of carbobenzoxyhydrazide, 9.86 gm (0.05 mole) of benzyl 2-pyridyl ketone and 100 ml of 95% ethanol is refluxed 6 hr. The reaction mixture is treated with decolorizing carbon and filtered. The heated filtrate is diluted with water to the cloud point. The mixture is cooled to room temeprature and then chilled in the refrigerator. The product is collected, washed with water and dried to yield 11.06 gm (64%) of the title compound having a melting point of 155.1° C.

Analysis Calcd: C, 73.04; H, 5.51; N, 12.17.
Found: C, 73.06; H, 5.71; N, 12.30.

The title compound is resynthesized employing the above procedure, at about 6x scale-up to yield 58.4 gm (60%) having a melting point of 158.7° C.
Found: C, 72.73; H, 5.43; N, 11.96.

Procedure 13

Preparation of 1,1,-dimethylethyl (α-4-pyridinylbenzylidene)carbazate, Compound 81

To 6.61 gm (0.05 mole) of t-butylcarbazate dissolved in 100 ml of warm water is added 9.16 gm (0.05 mole) of 4-benzoylpyridine in 30 ml of ethanol. The mixture is refluxed 7 hr. Cooling several weeks yields 1.77 gm (12%) of the title compound having a melting point of 134.5° C.

Analysis Calcd: C, 68.69; H, 6.40; N, 14.14.
Found: C, 69.06; H, 6.44; N, 14.22.

Procedure 14

Preparation of methyl (4-pyridinylmethylene)carbazate hydrate, Compound 83

A solution of 2.70 gm (0.03 mole) of methyl carbazate, 3.21 gm (0.03 mole) of 4-pyridinecarboxaldehyde and 50 ml of anhydrous methanol if refluxed 8 hr. The hot solution is filtered. The filtrate is diluted with water to the cloud point and cooled to room temperature. The mixture is chilled in the refrigerator. The crystals are collected, washed with water and dried to yield 5.87 gm (99%) of the title compound having a melting point of 159.6° C. (decomp.).

Analysis Calcd: C, 52.32; H, 5.18; N, 22.89.
Found: C, 52.70; H, 5.03; N, 22.81.

Procedure 15

Preparation of benzyl (4-pyridinylmethylene)carbazate, Compound 84

A mixture of 8.31 gm (0.05 mole) of carbobenzoxyhydrazide, 5.36 gm (0.05 mole) of 4-pyridinecarboxaldehyde and 100 ml of 95% ethanol is refluxed 4 hr. The hot solution is filtered. The filtrate is cooled to room temperature and then chilled in the refrigerator. The cream crystals are collected and dried to give 9.47 gm (74%) of the title compound having a melting point of 133.8° C.

Analysis Calcd: C, 65.88; H, 5.10; N, 16.47.
Found: C, 65.49; H, 5.07; N, 16.54.

Procedure 16

Preparation of diphenylmethyl (4-pyridinylmethylene)carbazate, Compound 86

To 24.11 gm (0.1 mole) of benzhydryl carbazate in 200 ml of warm absolute ethanol is added 10.66 gm (0.1 mole) of 4-pyridinecarboxaldehyde in 75 ml of absolute ethanol. The mixture is refluxed 7 hr and cooled. The solvent is removed in vacuo. Recrystallization from ethanol/Skellysolve B yields 26.03 gm (78.5%) of the title compound having a melting point of 159°–160° C.

Analysis Calcd: C, 72.49; H, 5.17; N, 12.68.
Found: C, 72.39; H, 5.36; N, 12.77.

The title compound is resynthesized using the above procedure at a 5X scale-up to yield 137.5 gm (41%) of the title compound having a melting point of 158°–159° C.

Found: C, 72.44; H, 5.10; N, 12.46.

Procedure 17

Preparation of diphenylmethyl (4-pyridinylmethylene)carbazate monohydrate, Compound 87

To 10.89 gm (0.045 mole) of benzhydryl carbazate in 100 ml of warm ethanol is added 4.82 gram (0.045 mole) of 4-pyridinecarboxaldehyde in 50 ml of ethanol. The mixture is refluxed 4.5 hr and cooled. The solvent is removed in vacuo to give the crude product. Recrystallization of the crude material from ethanol yields 14.6 gm (93%) of the title compound having a melting point of 96.9° C.

Analysis Calcd: C, 68.77; H, 5.44; N, 12.03.
Found: C, 69.07; H, 5.42; N, 11.50.

Procedure 18

Prepation of ethyl [1-(4-pyridinyl)propylidene]carbazate, Compound 90

A solution of 4.05 gm (0.03 mole) of 4-propionylpyridine, 3.12 gm (0.03 mole) of ethyl carbazate and 100 ml of absolute ethanol is refluxed 6 hr. The hot solution is filtered. The filtrate is diluted with water to the cloud point. The mixture is cooled at room temperature and then chilled in the refrigerator to give crystals which are collected, washed with Skellysolve B and dried to yield 3.25 gm (49%) of the title compound having a melting point of 147.1° C.

Analysis Calcd: C, 59.73; H. 6.79; N, 19.00.
Found: C, 59.83; H, 6.96; N, 18.99.

Procedure 19

Preparation of 1,1-dimethylethyl [1-(4-pyridinyl)propylidene]carbazate, Compound 91

A solution of 4.05 gm (0.03 mole) of 4-propionylpyridine, 3.96 gm (0.03 mole) of t-butylcarbazate and 100 ml of absolute ethanol is refluxed 6 hr. The reaction mixture is treated with decolorizing carbon and filtered. The filtrate yields crystals on cooling. The product is collected, washed with Skellysolve B and dried to yield 3.16 gm (40%) of the title compound having a melting point of 170.1° C.

Analysis Calcd: C, 62.65; H, 7.63; N, 16.87.
Found: C, 62.67; H, 7.79; N, 17.05.

The title compound is resynthesized two times, employing the above procedure at a scale-up of 2.3X and 11.56X to yield 11.9 gm (68%) and 57.5 gm (67%), respectively.

Analysis Found: C, 62.60; H, 7.67; N, 16.89; mp 183.0° C.
Found: C, 62.69; H, 7.59; N, 16.85; mp 181.5°–182° C.

Procedure 20

Preparation of methyl [1-(4-pyridinyl)propylidene]carbazate, Compound 93

A solution of 4.05 gm (0.03 mole) of 4-propionylpyridine, 2.70 gm (0.03 mole) of methyl carbazate and 100 ml of absolute ethanol is refluxed 6 hr. The solution is evaporated in vacuo to give a solid. The crude product is crystallized from ethyl acetate/Skellysolve B to yield 3.90 gm (63%) of the title compound having a melting point of 216.2° C. (decomp.).

Analysis Calcd: C, 57.97; H, 6.28; N, 20.29.
Found: C, 57.67; H, 6.35; N, 20.58.

Procedure 21

Preparation of phenyl[1-(4-pyridinyl)ethylidene]carbazate, Compound 94

A solution of 5.66 gm (0.03 mole) of phenyl carbazate hydrochloride, 3.63 gm (0.03 mole) of 4-acetylpyridine and 50 ml of ethanol is refluxed 2 hr. The solution is cooled and evaporated to dryness in vacuo to give an oil. The oil is triturated with ethyl acetate-methanol to afford a solid. The solid is dissolved in 50 ml of water and treated with 50 ml water containing 5 gm sodium carbonate. A gummy solid separates which solidifies on standing. The crude product is collected and crystallized from ethyl acetate-Skellysolve B to yield 4.13 gm (54%) of the title compound having a melting point of 120.4° C. (decomp.).

Analysis Calcd: C, 65.88; H, 5.10; N, 16.47.
Found C, 66.01; H, 5.12; N, 16.33.

Procedure 22

Preparation of phenyl[1-(4-pyridinyl)ethylidene]carbazate monohydrochloride, Compound 95

A mixture of 12.11 gm (0.1 mole) of 4-acetylpyridine, 18.85 gm (0.1 mole) of phenyl carbazate hydrochloride and 250 ml of absolute ethanol is refluxed 6 hr and cooled. The reaction mixture is evaporated to drynes in vacuo to give a rose-colored solid. The crude product is crystallized from absolute ethanol to yield 28.13 gm (97%) of the title compound having a melting point of 159.1° C.

Analysis Calcd: C, 57.63; H, 4.80; Cl, 12.18; N, 14.41.
Found: C, 57.84; H, 4.86; Cl, 11.87; N, 14.25.

Procedure 23

Preparation of ethyl (α-4-pyridinylbenzylidene)carbazate, Compound 96

A mixture of 9.16 gm (0.05 mole) of phenyl 4-pyridyl ketone, 5.21 gm (0.05 mole) of ethylcarbazate and 75 ml of glacial acetic acid is heated at 100° C. for 8 hr. The acetic acid is removed in vacuo. The residue is slurried with ethyl ether and collected to yield 5.76 gm (39%) of the title compound having a melting point of 188.7° C.

Analysis Calcd: C, 67.91; H, 5.58; N, 15.61.
Found: C, 67.39; H, 5.61; N, 15.36.

Procedure 24

Preparation of 5-methyl-2-(1-methylethyl)cyclohexyl [1-(4-pyridinyl)ethylidene]carbazate, Compound 97

A solution of 6.43 gm (0.03 mole) of 1-methylcarbazate, 3.63 gm (0.03 mole) of 4-acetylpyridine and 100 ml of absolute ethanol is refluxed 3 hr. The solvent is evaporated in vacuo to give a solid. The product is crystallized from ethyl acetate/Skellysolve B to yield 4.07 gm (43%) of the title compound having a melting point of 188.2° C.

Analysis Calcd: C, 68.14; H, 8.52; N, 13.25.
Found: C, 67.76; H, 8.59; N, 13.24

Procedure 25

Preparation of 1,1-dimethylethyl [1-(4-pyridinyl)pentylidene]carbazate, Compound 98

A solution of 11.2 gm (0.0751 mole) of n-butyl 4-pyridyl ketone, 9.80 gm (0.0741 mole) of butyl carbazate, 100 ml of tetrahydrofuran and 0.1 gm of p-toluenesulfonic acid is refluxed 17 hr. The reaction mixture is poured into 300 ml of ice and water with stirring to give a white solid. The crude product is collected, washed with water and dried. The crude product is crystallized from acetone/hexane to yield 9.27 gm (44%) of the title compound having a melting point of 156.2° C.

Analysis Calcd: C, 64.98; H, 8.30; N, 15.16.
Found: C, 64.89; H, 8.50; N, 14.87.

Procedure 26

Preparation of ethyl [1-(4-pyridinyl)pentylidene]carbazate, Compound 99

A mixture of 8.3 gm (0.055 mole) of n-butyl 4-pyridinyl ketone, 6.1 gm (0.059 mole) of ethyl carbazate and 150 ml of absolute ethanol is refluxed 17 hr. A Tlc (3%

MeOH/CH$_2$Cl$_2$ on Silica gel) shows 50% starting material remaining. p-Toluenesulfonic acid (0.3 gm) is added and the reaction mixture refluxed 17 hr more. Tlc shows no remaining starting materials. The reaction is concentrated in vacuo. The residue is slurried with water and the solid collected, washed with water and dried. Crystallization yields 7.41 gm of the title compound having a melting point of 102.1° C.

Analysis Calcd: C, 62.63; H, 7.68; N, 16.85.
Found: C, 62.51; H, 7.73; N, 17.39.

Procedure 27

Preparation of phenyl (4-pyridinylmethylene)carbazate monohydrochloride, Compound 101

A solution of 6.43 gm (0.06 mole) of 4-pyridinecarboxaldehyde, 11.31 gm (0.06 mole) of phenyl carbazate hydrochloide and 300 ml of 95% ethanol is refluxed 4 hr. The reaction mixture is evaporated to dryness. The crude product is suspended in 200 ml of boiling absolute ethanol and sufficient methanol added to give a solution. The hot solution is filtered, the filtrate cooled to room temperature and then chilled in the freezer. The crystals are collected, washed with Skellysolve B and dried to yield 11.0 gm (66%) of the title compound having a melting point of 224.4° C. (decomp.)

Analysis Calcd: C, 56.22; H, 4.32; Cl, 12.79; N, 15.14.
Found: C, 56.13; H, 4.46; Cl, 12.62; N, 15.35.

Procedure 28

Preparation of ethyl [1-(4-pyridinyl)ethylidene]carbazate 1-oxide, Compound 109

A solution of 5.48 gm (0.04 mole) of 4-acetylpyridine1-oxide, 4.16 gm (0.04 mole) of ethylcarbazate and 100 ml of absolute ethanol is refluxed 6 hr. The solution is evaporated in vacuo to give a solid. The crude product is crystallized from ethyl acetate/ethanol to yield 6.47 gm (73%) of the title compound having a melting point of 220.1° C.

Analysis Calcd: C, 53.81; H, 5.83; N, 18.83.
Found: C, 53.63; H, 5.78; N, 18.63.

Procedure 29

Prepatation of phenyl [1-(4-pyridinyl)butylidene]carbazate 1-oxide, Compound 112

To 6.61 gm (0.04 mole) of 4-butyrylpyridine 1 -oxide in ca. 100 ml of ethanol is added 7.54 gm (0.04 mole) of phenyl carbazate hydrochloride and the mixture heated on the steam bath for a total of 6 hr. After 4 hr the solution is allowed to evaporate to less than 100 ml and cooled. The mixture is chilled in the freezer to yield 5.17 gm (43%) of the title compound having a melting point of 206.5° C. (decomp).

Analysis Calcd: C, 63.99; H, 6.25; N, 13.92.
Found: C, 64.20; H, 5.72; N, 14.04.

Procedure 30

Preparation of phenyl [1-(4-pyridinyl)ethylidene]carbazate 1-oxide monohydrochloride, Compound 118

A mixture of 5.48 gm (0.04 mole) of 4-acetylpyridine 1-oxide, 7.54 gm (0.04 mole) of phenyl carbazate hydrochloride and 100 ml of absolute solid. The crude product is crystallized from ethanol/ethyl acetate to yield 8.45 gm (78%) of the title compound having a melting point of 196.8° C.

Analysis Calcd: C, 54.63; H, 4.55; Cl, 11.54; N, 13.66.
Found: C, 54.27; H, 4.66; Cl, 11.58; N, 13.44.

Procedure 31

Preparation of benzyl [1-(4-pyridinyl)ethylidene]carbazate 1-oxide hydrate, Compound 119.

A mixutre of 5.48 gm (0.04 mole) of 4-acetylpyridine-1-oxide, 6.64 gm (0.04 mole) of benzyl carbazate and 200 ml of absolute ethanol is refluxed 7 hr. The solvent is removed in vacuo to give a solid. The crude product is recrystallized from isopropyl alcohol to yield 10.14 gm (87%) of the title compound having a melting point of 219.4° C. (decomp).

Analysis Calcd: C, 61.98; H, 5.37; N, 14.46; H$_2$O, 1.86.
Found: C, 61.86; H, 5.76; N, 13.93; H$_2$O, 1.73.

Procedure 32

Preparation of 1,1-dimethylethyl [1-(4-pyridinyl)ethylidene]carbazate 1-oxide, Compound 120

A mixture of 5.48 gm (0.04 mole) of 4-acetylpyridine 1-oxide, 5.29 gm (0.04 mole) of butyl carbazate and 100 ml of absolute ethanol is refluxed 7 hr. The reaction mixture is evaporated to dryness in vacuo to furnish a solid. The crude product is crystallized from ethanol to yield 4.5 gm (45%) of the title compound having a melting point of 214.3° C.

Analysis Calcd: C, 57.37; H, 6.77; N, 16.73.
Found: C, 57.29; H, 6.76; N, 16.77.

Procedure 33

Preparation of 4-trifluoromethylbenzoic acid [1-(4pyridinyl)ethylidene]hydrazide, Compound 121

A mixture of 2.97 gm (0.0245 mole) of 4-acetylpyridine, 5.0 gm (0.0245 mole) of 4-trifluoromethylbenzhydrazide and 100 ml of absolute ethanol is refluxed for 6 hr. The hot solution is filtered. The filtrate is diluted with water to the cloud point, cooled to room temperature and chilled. The crystals which separate are collected, washed with water and dried to yield 6.29 gm (84%) of the title compound having a melting point of 198.4° C.

Analysis Calcd: C, 58.63; H, 3.91; N, 13.68.
Found: C, 58.48; H, 4.05; N, 13.76.

Procedure 34

Preparation of acetic acid [1-(4-pyridinyl)ethylidene]hydrazide, Compound 136

A mixture of 2.22 gm (0.03 mole) of acetic acid hydrazide, 3.63 gm (0.03 mole) of 4-acetylpyridine and 100 ml of absolute ethanol is refluxed 2 hr. The hot solution is filtered. The filtrate is diluted with water to the cloud point. The mixture is cooled to room temperature and then chilled in the refrigerator. The product is collected, washed with water and dried to yield 3.63 gm (69%) of the title compound having a melting point of 178.1° C.

Analysis Calcd: C, 61.02; H, 6.21.
Found C, 61.22; H, 6.24.

The title compound is remade, with a scale-up of 3X, using the above procedure to yield 34.4 gm (66%) having a melting point of 177.5°-178.5° C.

Analysis Calcd: C, 61.02; H, 6.21; N, 23.73.
Found: C, 60.99; H, 6.52; N, 23.88.

Procedure 35

Preparation of (2,4,5-trichlorophenoxy)acetic acid [1-(4-pyridinyl)ethylidene]hydrazide, Compound 137

A solution of 5.39 gm (0.02 mole) of 2,4,5-trichlorophenoxyacetic acid hydrazide, 2.42 gm (0.02 mole) of 4-acetylpyridine, 125 ml of dioxane and 2 ml of acetic acid is refluxed 4 hr. The hot solution is filtered. The filtrate is diluted with water until cloud point. The mixture is cooled to room temperature and then chilled in the refrigerator. The product is collected to yield 6.24 gm (83%) of the title compound having a melting point of 227.4° C. (decomp).

Analysis Calcd: C, 48.32; H, 3.22; N, 11.28.
Found: C, 48.47; H, 3.28; N, 11.33.

Procedure 36

Preparation of benzoic acid [1,3-dioxan-5-yl)-3-pyridinylmethylene]hydrazide, Compound 421

Following the general method of procedure 56 and making non-critical variations, except overnight refluxing is required, 12 drops of concentrated hydrochloric acid is used and no methylene chloride extraction in the work-up is employed, 9.66 gm (0.05 mole) of 1,3-dioxan-5-yl 3-pyridyl ketone and 6.81 gm (0.05 mole) of benzhydrazide yeild 6.58 gm (42%) of the title compound having a melting point of 131.8° C.

Analysis Calcd: C, 65.68; H, 5.50; N, 13.50.
Found: C, 65.02; H, 5.57; N, 13.44.

Procedure 37

Preparation of formic acid [1-(4-pyridinyl)pentylidene]hydrazide, Compound 141

A solution of 14.26 gm (0.0956 mole) of n-butyl 4-pyridyl ketone, 5.70 gm (0.0956 mole) of formylhydrazine, 50 ml of THF, 30 ml of absolute ethanol and 0.1 gm of p-toluenesulfonic acid is refluxed 24 hr. The reaction is chilled to give a white solid which is collected and discarded. The filtrate is concentrated in vacuo to furnish a solid. This material is dissolved in methylene chloride. The methylene chloride solution is washed with saturated sodium bicarbonate solution; then brine. The organic layer is dried over magnesium sulfate and concentrated in vacuo in the presence of excess hexane to yield 5.14 gm (26%) of the title compound having a melting point of 143.4° C.

Analysis Calcd: C, 64.47; H, 7.33; N, 20.73.
Found: C, 64.47; H, 7.33; N, 20.73.

Procedure 38

Preparation of butyric acid [1-(4-pyridinyl)ethylidene]hydrazide oxalic acid salt, Compound 145

A mixture of 6.15 gm (0.03 mole) of butyric acid [1-(4-pyridinyl)ethylidene]hydrazide (Compound 144), 2.70 gm (0.03 mole) of oxalic acid and 100 ml of absolute ethanol is refluxed 3 hr. The mixture is cooled and then chilled in the refrigerator. Two crops of the product are collected and dried to yield 6.9 gm (78%) of the title compound having a melting point of 207.2° C.

Analysis Calcd: C, 52.88; H, 5.76; N, 14.24.
Found, C, 52.60; H, 6.13; N, 13.45.
Found: C, 52.47; H, 6.31; N, 13.13.

Procedure 39

Preparation of butyric acid [1-(4-pyridinyl)ethylidene]hydrazide 1-hydroxy-2-naphthoic acid salt, Compound 147

A mixture of 8.2 gm (0.04 mole) of butyric acid [1-(4-pyridinyl)ethylidene]hydrazide (Compound 144), 7.53 gm (0.04 mole) of 1-hydroxy-2-naphthoic acid and 100 ml of absolute ethanol is refluxed 7 hr. Cooling the reaction mixture to room temperature and then chilling yields a solid which is collected and dried to provide 13.67 gm (87%) of the title compound having a melting point of 158.7° C.

Analysis Calcd: C, 67.18; H, 5.85; N, 10.69.
Found: C, 67.06; H, 5.86; N, 10.71.

Procedure 40

Preparation of butyric acid [1-(4-pyridinyl)ethylidene]hydrazide phenoxyacetic acid salt, Compound 151

A mixture of 8.2 gm (0.04 mole) of butyric acid [1-4-pyridinyl)ethylidene]hydrazide (Compound 144), 6.09 gm (0.04 mole) of phenoxyacetic acid and 100 ml of absolute ethanol is refluxed 7.5 hr. The reaction mixture is evaporated to dryness in vacuo. The solid is crystallized from ethanol to yield 9.48 gm (66%) of the title compound having a melting point of 105.8° C.

Analysis Calcd: C, 63.87; H, 6.44; N, 11.76.
Found: C, 63.41; H, 6.54; N, 11.87.

Procedure 41

Preparation of cyclohexanecarboxyalic acid [1-(4-pyridinyl)ethylidene]hydrazide, Compound 159

A solution of 4.26 gm (0.03 mole) of cyclohexanecarboxylic acid hydrazide, 3.63 gm (0.03 mole) of 4-acetylpyridine and 100 ml of ethanol is refluxed 7 hr. The solvent is evaporated in vacuo to give a white solid. The product is crystallized from ethyl acetate to yield 5.38 gm (73%) of the title compound having a melting point of 195.3° C.

Analysis Calcd: C, 68.57; H, 7.76; N, 17.14.
Found: C, 68.54; H, 8.00; N, 17.27.

Procedure 42

Preparation of 2-methoxybenzoic acid (4-pyridinylbenzylidene)hydrazide monohydrochloride, Compound 285

To 9.16 gm (0.05 mole) of 4-benzolypyridine in 100 ml of absolute ethanol and 4.4 ml of (0.05 mol) concentrated hydrochloric acid (yellow solution) was added 8.31 gm (0.05 mole) of 2-methoxybenzylhydrazide. The reaction mixture was refluxed 12 hrs and filtered. The filtrate was concentrated to about ½ volume and cooled. The yellow crystals which formed were collected, worked with cold absolute ethanol and dried to give 17.4 gm (95%) of the title compound having a melting point of 242.1°.

Analysis Calcd: C, 65.31; H, 4.93; N, 11.42; Cl, 9.64.
Found: C, 65.08; H, 5.03; N, 11.53; Cl, 9.36.

Procedure 43

Preparation of cyclohexanecarboxylic acid [1-(4-pyridinyl)ethylidene]hydrazide 1-oxide, Compound 287

A mixture of 5.48 gm (0.04 mole) of 4-acetylpyridine 1-oxide, 5.68 gm (0.04 mole) of cyclohexanecarboxylic acid hydrazide and 100 ml of absolute ethanol is refluxed 4 hours. The reaction mixture is concentrated in vacuo to dryness to give a solid. The solid is crystallized from isopropanol to furnish 8.20 gm (79%) of the title compound; mp 245.3°.

Analysis Calcd: C, 64.37; H, 7.28; N, 16.09.
Found: C, 63.77; H, 7.55; N, 15.84.

Procedure 44

Preparation of butyric acid [1-pyridinyl)ethylidene]hydrazide 1-oxide hydrate, Compound 289

A mixture of 5.48 gm (0.04 mole) of 4-acetylpyridine 1-oxide, 4.09 gm (0.04 mole) of butyric acid hydrazide and 100 ml of absolute ethanol is refluxed 6 hours. The reactions mixture is evaporated in vacuo to give a solid. The crude product is crystallized from ethyl acetate/ethanol to yield 7.41 gm (84%) of the title compound; mp 209.7°.

Analysis Calcd: C, 59.25; H, 6.82; H, 18.85.
Found: C, 59.18; H, 6.94; N, 18.53.

Procedure 45

Preparation of cyclobutanecarboxylic acid [1-(4-pyridinyl)ethylidene]hydrazide, Compound 290

A mixture of 6.06 gm (0.05 mole) of 4-acetylpyridine, 5.7 gm (0.05 mole) of cyclobutanecarboxylic acid hydrazide, and 100 ml of absolute ethanol is refluxed 5 hours. The reaction mixture is evaporated in vacuo to give a solid. The product is crystallized from ethanol/ethylacetate/diethylether to give 2.92 gm (27%) of the title compound; mp 138.6°.

Analysis Calcd: C, 66.36; H, 6.91; N, 19.35.
Found: C, 65.97, H, 6.84; N, 19.44.

Procedure 46

Preparation of 4-nitrobenzoic acid [1-(4-pyridinyl)ethylidene]hydrazide, Compound 291

A mixture of 3.62 gm (0.02 mole) of p-nitrobenzhydrazide, 2.42 gm (0.02 mole) of 4-acetylpyridine and 100 ml of absolute ethanol is refluxed 3 hours. Sufficient dimethylformamide is added to the mixture at boiling to give a solution. The hot solution is filtered. The filtrate is diluted with water to the cloud point. The mixture is chilled in the refrigerator. The product is collected, washed with ether and dried to yield 4.46 gm (79%) of the title compound; mp 251.1°.

Analysis Calcd: C, 59.15; H, 4.23; N, 19.72.
Found: C, 59.24; H, 4.80; N, 19.79.

Procedure 47

Preparation of 2-methylcyclopropanecarboxylic acid [1-(3-pyridinyl)propylidene]hydrazide, Compound 313

A mixture of 8.0 gm (0.07 mole) of 2-methylcyclopropanecarboxylic acid hydrazide, 9.46 gm (0.07 mole) of ethyl-3-pyridyl ketone, 10 drops of glacial acetic acid and 100 ml of EtOH was refluxed 20 hr. Tlc (9:1 Skellysolve B/Ethyl acetate on silica gel) shows no remaining starting material. The reaction mixture was cooled to room temperature and evaporated in vacuo to give a liquid. The liquid solidified on standing. The solid was slurried in ether, collected and dried to give 4.77 gm (29%) of the title compound having a melting point of 137.3° C.

Analysis Calcd: C, 67.51; H, 7.41; N, 18.86.
Found: C, 66.99; H, 7.48; N, 18.08.

Proceudre 48

Preparation of 3-trifluoromethylbenzoic acid [1-(3-pyridinyl)propylidene]hydrazide, Compound 316

A mixture of 10.21 gm (0.05 mole) of 3-trifluoromethylbenzoic acid hydrazide, 6.76 gm (0.05 mole) of ethyl-3-pyridyl ketone, 10 drops of glacial acetic acid and 100 ml of absolute ethanol was refluxed 15 hr. The reaction mixture was diluted with water to the cloud point and cooled at room temperature than chilled in the refrigerator. The solids that separated were collected, washed with Skellysolve B and dried to give 11.88 gm (74%) of product having a melting point of 119.4° C.

Analysis Calcd: C, 59.81; H, 4.39; 13.07; F, 17.74.
Found: C, 59.65, H, 4.49; 13.14; F, 18.25.

Procedure 49

Preparation of acetic acid [1-(6-methyl-3-pyridinyl)ethylidene]hydrazide, Compound 327

A mixture of 6.76 gm (0.05 mole) of 2-methyl-5-acetylpyridine, 3.7 gm (0.05 mole) of acetic acid hydrazide and 100 ml of ethanol was refluxed 5 hr. The solution was diluted with Skellysolve B until cloudy. The mixture was cooled to room temperature and then chilled in the freezer. The product was collected, washed ith Skellysolve B and dried to afford 7.93 gm (83%) of the title compound having a melting point of 178.5° C.

Analysis Calcd: C, 62.81; H, 6.85; N, 21.97.
Found: C, 62.83; H, 6.83; N, 22.03.

Procedure 50

Preparation of 3-trifluoromethylbenzoic acid [1-(3-pyridinyl)ethylidene]hydrazide, Compound 301

A mxiture of 10.21 gm (0.05 mole) of 3-trifluoromethylbenzoic acid hydrazide, 100 ml of ethanol and 10 drops of glacial acetic acid was refluxed for 14 hr. The solution was cooled at room temperature and then chilled in the freezer. The product was collected, washed with water and dried to give 11.77 gm (77%) of white solid which had a melting point of 183.3° C.

Analysis Calcd: C, 58.64; H, 3.94; N, 13.67.
Found: C, 58.36; H, 4.08; N, 13.68.

Procedure 51

Preparation of 3-nitro-1-nepthalenecarboxylic acid [1-(4-pyridinyl)ethylidene]hydrazide, Compound 342

A mixture of 5.0 gm of (0.0216 mole) of 3-nitro-1-naphthalenecarboxylic acid hydrazide, 2.62 gm (0.0216 mole) of 4-acetylpyridine, 400 ml of ethanol, 100 ml of tetrahydrofuran, and 20 drops of glacial acetic acid was refluxed 10 hr. The hot solution was filtered. The filtrate was cooled to room temperature and then chilled. The product was collected, washed with Skellysolve B and dried to furnish 6.31 gm (87%) of the title compound having a melting point of 228.5° C.

Analysis Calcd: C, 64.67; H, 4.22; N, 16.75.
Found: C, 64.56; H, 4.55; N, 16.29.

Procedure 52

Preparation of nicotinic acid (phenyl-4-pyridinylmethylene)hydrazide, Compound 353

A mixture of 9.16 gm (0.05 mole) of 4-benzoyl pyridine, 6.86 gm (0.05 mole) of nicotinic acid hydrazide, 100 ml of ethanol and 4.4 ml of concentrated hydrochloric acid was refluxed 16 hr. The reaction mixture was cooled to room temperature. An equal volume of water was added containing 5.4 gm (0.05 mole) of sodium carbonate. The mixture was placed in the refrigerator. The product which separated was collected, washed with water and dried to give 8.21 gm (54%) of the title compound having a melting point of 74.0° C.

Analysis Calcd: C, 71.51; H, 4.67; N, 18.13.
Found: C, 71.66; H, 4.98; N, 18.20.

Procedure 53

Preparation of formic acid [1-(3-chloro-4-pyridinyl)ethylidene]hydrazide, Compound 394

A mixture of 6.30 gm (0.0405 mole) of 4-acetyl-3-chloropyridine, 2.46 gm (0.041 mole) of formic acid hydrazide and 100 ml of ethanol was refluxed 18 hr. The mixture was chilled in the freezer to give a solid which was collected in two crops. The product was purified by chromotography [keiselgel 60 (230–400 mesh)] and eluting with 5% methanol/methylene chloride to give 2.56 gm (32%) of white flakes which have a melting point of 175.2° C.

Analysis Calcd: C, 48.62; H, 4.08; N, 21.26; Cl, 17.94.
Found: C, 48.29; H, 4.14; N, 20.92; Cl, 17.93.

Procedure 54

Preparation of butyric acid [1-(3-chloro-4-pyridinyl)ethylidene]hydrazide, Compound 395

A mixture of 5.20 gm (0.0335 mole) of 4-acetyl-3-chloropyridine, 3.43 gm (0.0336 mole) of butyric acid hydrazide and 100 ml of ethanol was refluxed 18 hr. The mixture was chilled in the freezer. The solid which separated was collected to give 2.01 gm (25%) of white solid having a melting point of 103.8° C.

Analysis Calcd: C, 55.12; H, 5.89; N, 17.53; Cl, 14.79.
Found: C, 54.97; H, 5.92; N, 17.42; Cl, 14.83.

Procedure 55

Preparation of cyclopropanecarboxylic acid [1-(6-chloro-3-pyridinyl)ethylidene]hydrazide, Compound 414

Following the general method of procdure 53 and making non-critical variations, except the product was purified by recrystallization from absolute ethanol rather than by chromatography, 5.25 gm (0.0337 mole) of 3-acetyl-6-chloropyridine and 3.40 gm (0.034 mole) of cyclopropanecarboxylic acid hydrazide yield 6.52 gm (81%) of the title compound having a melting point of 218.1° C.

Analysis Calcd: C, 55.59; H, 5.09; N, 17.68; Cl 14.92.
Found: C, 55.40; H, 5.18; N, 17.56; Cl, 15.02.

Procedure 56

Preparation of ethyl [(1,3-dioxan-5-yl)-3-pyridinylmethylene]carbazate, Compound 422

To 8.30 gm (0.043 mole) of 1,3-dioxan-5-yl-3-pyridyl ketone in 100 ml of absolute ethanol is added 4.47 gm (0.043 mole) of ethyl carbazate and one equivalent of concentrated hydrochloric acid. The reaction mixture is refluxed for 8 hr, then treated with activated charcoal and filtered hot. The filtrate is concentrated to about 100 ml volume and one equivalent of sodium carbonate in warm water added to give a final Ph of 8. The solution is concentrated to approximately 100 ml total volume (nearly all ethanol stripped) on the rotoevaporator. The aqueous solution is extracted with 3×75 ml methylene chloride. The combined chloride extracts are washed with brine, dried over sodium sulfate, then evaporated to give a solid. The product is crystallized from absolute ethanol to give 4.97 gm (40%) of the title compound having a melting point of 131.8° C.

Analysis Calcd: C, 55.91; H, 6.14; N, 15.04.
Found: C, 55.62; H, 6.36; N, 14.70.

Procedure 57

Preparation of propanoic acid [(1,3-dioxan-5-yl)-4-pyridinyl-methylene]hydrazide, Compound 433

Following the general method of procedure 56 and making non-critical variations, except 12 drops of glacial acetic acid is used and extraction with methylene chloride in the work-up is not required, 8.36 gm (0.0433 mole) of 1,3-dioxan-5-yl 4-pyridyl ketone and 3.81 gm (0.0433 mole) of propanoic acid hydrazide yields 3.04 gm (27%) of the title compound having a melting point of 125.7° C.

Analysis Calcd: C, 59.30; H, 6.51; N, 15.60.
Found: C, 58.92; H, 6.63; N, 15.45.

Procedure 58

Preparation of ethyl [(1,3-dioxan-5-yl)-4-pyridinylmethylene]carbazate, Compound 431

Following the general method of procedure 56 and making non-critical variations, except extraction with methylene chloride in the work-up is not required and the product is crystallized from aqueous ethanol, 8.30 gm (0.043 mole) of 1,3-dioxan-5-yl 5-pyridyl ketone and 4.47 gm (0.0430 mole) of ethyl carbazate yield 6.13 gm (55%) of the title compound in two crops having melting points of 64.9° C. and 65.0° C.

Analysis Calcd: C, 55.91; H, 6.14; N, 15.04
Found: C, 55.23; H, 5.95; N, 14.99.

Procedure 59

Preparation of benzoic acid [1,3-dioxan-5-yl)-4-pyridinylmethylene]hydrazide, monohydrochloride, Compound 423

Following the general method of procedure 56 and making non-critical variations, except no neutralization with sodium carbonate is used and extraction with methylene chloride in the work-up is not required, 4.23 gm (0.0219 mole) of 1,3-dioxan-5-yl 4-pyridyl ketone and 2.98 gm (0.0219 mole) of benzhydrazide yield 5.29 gm (77%) of the title compound having a melting point of 157.7° C.

Analysis Calcd: C, 58.71; H, 5.22; N, 12.08; Cl, 10.19.
Found: C, 58.37; H, 5.15; N, 11.97; Cl, 10.58.

The compounds prepared according to Procedures 1–59 are tabulated in Table A along with other illustrative compounds of the invention prepared following the general procedure indicated (Procedures 1–59) and making non-critical variations, except starting with the appropriate pyridyl ketone (II) and acyl hydrazide/carbazate (III).

Compounds 404, 406–407, 418 and 427–429 can be prepared by following the general procedure indicated in Table A and making non-critical variations, except starting with the appropriate pyridyl ketone (II) and acyl hydrazide/carbazate (III).

The pyridinyl acylhydrazones of this invention are effective against worms, particularly parasitic worms of warm-blooded animals and more particularly helminth parasites in ovines (sheep) and bovines (cattle).

Although a significant number of the pyridinyl acylhydrazones of this invention have failed to demonstrate significant activity against *Nematospiroides dubius* in mice or *Caenorhabditis elegans in vitro*, observations in sheep experimentally infected with *Haemonchus contortus* in accordance with Procedure I, generally confirm anthelmintic activity at 100 mg/kg of body weight upon oral and/or parenteral administration as set forth in Table I. Pyridinyl acylhydrazones which are toxic at 100 mg/kg of body weight are expected to exhibit anthelmintic activity at a lower non-toxic dose, see for example compound No. 139. Further observations in sheep naturally infected with various helminths also confirmed broad-spectrum anthelmintic activity of various pyridinyl acylhydrazones of this invention. See Procedure II and the results as set forth in Table II.

Procedure No. I

In individual experiments all sheep are treated identically, however non-critical variations occur between experiments. All of the sheep used in this procedure are treated twice with levamisole hydrochloride orally at 8 mg/kg or once each with ivermectin parenterally at 200 μ/kg and levamisole hydrochloride orally at 8 mg/kg. The second treatment in each case is administered 4–7 days after the first treatment. Two weeks after the second treatment all sheep are inoculated per os with −3,500 to −7,500 infective larvae of *H. contortus*. Rectal fecal samples are taken from each sheep 26–41 days post-inoculation (PI), and these samples are examined for eggs of *H. contortus* using the McMaster counting chamber technique. All sheep harboring good infections of *H. contortus* are randomly allocated to a treatment group; those which do not exhibit suitable infections are dropped from the study. One-three days later on days 27–42 PI each sheep remaiing in the study (excluding the nontreated controls) is treated with a test compound (orally or parenterally at 100 mg/kg unless indicated otherwise) or a standard (levamisole hydrochloride orally at 8 mg/kg) or is used as untreated control. All sheep received food and water ad lib. throughout the experiment.

Prior to administration, all solid compounds are finely ground using a mortar and pestle. Oral compounds are suspended in 2014 30 ml of sterile vehicle #98 (each ml contains: carboxymethylcellulose=10 mg, polysorbate80 −4 mg, propylparaben - 0.42 mg) using a sonicator and administered along with a tap water wash via a stomach tube. The parenteral compounds are similarly suspended in 20–30 ml of the sterile vehicle and given by intraperitoneal injection using a 13 gauge, 2 inch needle and a 50 ml syringe. All test compounds are given to a single sheep/route of administration. Two or more sheep are treated with levamisole hydrochloride and five are used as nontreated controls. All animals are monitored for signs of toxicity following treatment.

The sheep are sacrificed 7–12 days after treatment (days 35–49 PI), and the abomasum is ligated and removed from each sheep. Each abomasum is longitudinally sectioned and rinsed into an 80 mesh sieve. Sieve contents are collected in individual containers and fixed in formol-alcohol. Later each sample is transferred to a 1000 or 2000 ml beaker and the volume brought to 400–1000 ml with tap water. The total number of worms in a 40–100 ml aliquot (10%) is determined. When no worms are found in the 10% aliquot, the entire sample is examined. Total worm number/sheep and percentage clearance for each treatment are calculated. Percentage clearance for a particular test compound in a given trial is determined according to the following formula:

Percentage Clearance (Test Compound) =

[(Mean number of worms recovered from nontreated control sheep − Number of worms recovered from treated sheep)/Mean number of worms recovered from nontreated control sheep] × 100.

Sheep which die within 24 hr following treatment are not examined for worms, while any that die between 24 hr post-treatment and necropsy are examined in an identical manner as that described above. The results of various trials are combined and reported in Table I as percentage clearance.

Procedure No. II

Parasitized sheep are randomly assigned to groups of five animals based on parasitic burden, weight, sex, and farm origin. Sheep are double ear-tagged, weighed, housed in a barn in community pens, fed hay supplemented with calf starter pellets or ½ lb corn/head/day. Water was given ad lib. Animals were allowed to acclimate for one-two weeks prior to treatment.

Each group of sheep receives a test compound either orally or parenterally at a dosage rate of 100 mg/kg. A group of sheep is treated with 8 mg/kg of levamisole hydrochloride and another group serves as an untreated control group. Orally administered compounds are suspended in 20–30 ml of sterile vehicle TM 98 (each ml contains: carboxymethylcellulose—10 mg, polysorbate80 −4 mg, propylparaben—0.42 mg), using a sonicator and administered along with a tap water wash via a stomach tube. For parenteral administration, compounds are similarly suspended in 20–30 ml of the sterile vehicle and given by intraperitoneal injection using a 13 gauge, 2 inch needle and a 50 ml syringe. Following treatment, all animals are observed for signs of toxicity.

The number and classification of helminth eggs per gram of feces (e.p.g.) are determined for each sheep during the acclimation period and in some cases at necropsy. Egg counts are made using the McMaster counting chamber technique and rectal fecal samples. Animals dying during the 24 hours immediately folowing dosing are not subjected to necropsy. Sheep that die 1–6 days posttreatment are posted and complete worm counts performed. All remaiing animals are sacrificed on days 7–8 posttreatment; equal numbers of sheep are sacrificed from each group on each day when necropsy requires more than one day. Each sheep is euthanised and bled out prior to opening the abdominal cavity. Ligatures are placed at the reticulo-omasal junction, the pyloric valve, and the ileo-cecal junction. The abomasum and small intestine are freed of fat and mesenteric attachments, longitudinally opened, and their contents placed in individual containers. The mucosal surface of each is washed with tap water, rubbed clean, and rinsed several times. Washings and ingesta for each organ are made up to 1 or 5 liters and a 10 or 20% aliquot in formalin is stored for later examination. The cecum, large intestine, and colon are freed of mesenteric attachments, each is longitudinally opened, and their contents washed, collected, and made up to 1 or 5 liters in 10% formalin. A 20% aliquot or the entire sample is stored. All carcasses are incinerated.

Ten percent of the total contents collected from the abomasum and small intestine and 10% or the entire contents of the large intestine, cecum, and colon are examined under stereoscopic magnification (40X). All worms are identified to genus and in some instances species. Separate adult and larval counts are determined.

The mean percentage clearance against specific helminths in the test sheep is calculated by subtracting the mean number of helminths observed in the treated sheep at necropsy from the mean number observed in the nontreated controls at necropsy, dividing the remainder by the latter mean number and multiplying by 100. The mean percentage clearances against the various helminths identified in the test sheep are calculated. The results from various trials for particular pyridinyl acylhydrazones of Formula I are combined and set forth in Table II. From an evaluation of the test results set forth in Tables I and II, it is clear that the pyridinyl acylhydrazones of this invention are efficacious, broad-spectrum anthelmintic agents.

Eight pyridinyl acylhydrazones; Benzoic acid [1-(3-pyridinyl)ethylidene]hydrazide, butyric acid [1-(4-pyridinyl)ethylidene]hydrazide, butyric acid (4-pyridinylmethylene)hydrazide, 4-ethoxybenzoic acid [1-(4-pyridinyl)ethylidene]hydrazide, 2-methylpropionic acid [1-(4-pyridinyl)ethylidene]hydrazide, 3-cyclohexanepropionic acid [1-(4-pyridinyl)ethylidene]-hydrazide 1-oxide, formic acid [1-(4-pyridinyl)ethylidene]hydrazide 1-oxide and ethyl (2-pyridinylmethylene)carbazate (Compounds 2, 144, 153, 16, 275, 160, 203 and 73); have been selected as representative of the class and the test results from various trials of the foregoing compounds are combined and set forth in Table IIA.

4-Ethoxybenzoic acid [1-(4-pyridinyl)ethylidene]hydrazide (Compound #16) has been tentatively identified for further evaluation in sheep while 2-methoxypropionic acid [1-(4-pyridinyl)ethylidene]hydrazide (Compound #275) has been tentatively identified for further evaluation in cattle.

The results of a multidose study of butyric acid [1-(4-pyridinyl)ethylidene]hydrazide, compound 144, are set forth in Table III. Five sheep were used for each dosage level, medicated and unmedicated controls in accordance with Procedure III.

Procedure III

Forty (40) sheep were selected from a flock of forty-six (46) pastured animals which had been placed in concrete-floored pens and allowed to acclimate for 12 days. The animals were selected and allocated (5/group) on the basis of weight, sex, fecal egg count, and number of parasite species observed in the fecal egg counts. The animals were treated two days after grouping. Throughout the study, lambs were fed alfafa hay and given water ad lib.

One group of lambs each (Groups 1–6, respectively) received 100, 50, or 25 mg of compound 144 per kg of body weight by either an oral or parenteral route. Lambs in the remaining two groups (7 and 8, respectively) received a standard (levamisole hydrochloride, 8 mg/kg orally) treatment or served as nontreated controls. Groups 1, 2 and 4 each had one sheep die after allocatino to groups and prior to treatment. In addition, one lamb in Group 4 was not included in the data for that group because the animal was moribund shortly after treatment and it was felt that his response was altered significantly by his condition at the time of treatment. One lamb in Group 5 and two lambs in Group 8 died following treatment, but egg and worm counts taken at the time of death were considered with data taken at necropsy for the remaining animals in each of these groups.

Helminth Egg Counts

The number and species of helminth eggs per gram of feces (e.p.g.) were determined for each lamb on day 0–2 of the acclimation period, on the day of treatment, and at necropsy. Egg counts were made using the double centrifugal flotation technique and rectal fecal samples.

Necropsy

All lambs were necropsied on day 7 posttreatment. Each animal was euthanized prior to opening the abdominal cavity. Ligatures were placed at the reticulo-omasal junction, the pyloric valve, and the ileo-cecal junction. Contents of the abomasum and small intestine were placed in individual jars and preserved with 10% formalin, while both organs were incubated separately in a physiological saline solution for 6–8 hours at 37° C. Following the incubation period, both organs were washed, and then the wash plus the digest for each were added together and fixed with 10% formalin. The combined cecum, large intestine, and colon contents were washed numerous times using a 100 mesh screen with openings of 0.53 mm and then fixed in 10% formalin. All carcasses were incinerated.

Helminth Counts

Aliquots from each abomasum and small intestine totaling 10% for contents and 20% for digests plus each total cecum, large intestine, colon sample were examined under stereoscopic magnification (15x), and all worms which were found were collected and stored. Worms were later identified to species and stage of development (L4, L5, or adult). L5's were those worms which possessed adult reproductive organs without eggs in the uterus or darkened spicules. Few immature worms were recovered and, therefore, only adult worms were considered.

Signs of toxicosis were observed following treatment in animals given the high dosage of Compound No. 144 by either route or the medium dosage administered parenterally. Discomfort persisted in affected lambs for several hours.

DETAILED DESCRIPTION (cont'd)

The pyridinyl acylhydrazones of Formula I (IA, IB, IC, ID or IE) can be used as the pure compounds or as mixtures of pure compounds but for practical reasons the compounds are preferably formulated as anthelmintic compositions and administered as a single or multiple dose, alone or in combination with other anthelmintics (e.g. avermectins, benzimidazoles, levamisole, praziquantel, etc.). For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity. In addition, the active compound(s) can be administered topically to the animal in a conventional pour-on formula.

Pure compounds, mixtures of the active compounds, or combinations thereof with a solid carrier can be administered in the animal's food, or administered in the form of tablets, pills, boluses, wafers, pastes, and other conventional unit dosage forms, as well as sustained-/controlled release dosage forms which deliver the active compound over an extended period of days, weeks or months. All of these various forms of the active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal feed to about 90 or 95 percent or more in a pill or capsule. In the latter form, one might use no more carrier than sufficient to bind the particles of active compound.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg per kg body weight for each 100 lb pig in its daily ration.

A solid diluent carrier need not be a homogenous entity, but mixtures of different diluent carriers can include small proportions of adjuvants such as water; alcohols; protein solutions and suspensions like skimmed milk; edible oils; solutions, e.g., syrups; and organic adjuvants such as propylene glycols, sorbitol, glycerol, diethyl carbonate, and the like.

The solid carrier formulations of the inventions are conveniently prepared in unit dosage forms, to facilitate administration to animals. Accordingly, several large boluses (about 20 g weight) amounting to about 54 g of active compound would be required for a single dosage to a 900 lb horse at a dosage rate of 50 mg/kg of body weight. Similarly, a 60 lb lamb at a dosage rate of 100 mg/kg of body weight would require a pill, capsule, or bolus containing about 2.7 g of active compound. A small dog, on the other hand, weighing about 20 lbs. would require a total dosage of about 225 mg at a dosage rate of 25 mg/kg of body weight. The solid, unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that a dose of 100 mg/kg of body weight in sheep of various pyridinyl acylhydrazones of this invention will effectively combat a wide variety of parasites. Much lower effective dosages are contemplated, e.g., in the range of 1 to 75 mg/kg of body weight.

In other animals, and for other kinds of parasitic worms, definitive dosages can be proposed. Contemplated are dosage rates of about 1 mg to about 800 mg/kg of body weight. A preferred, contemplated range of dosage rates is from about 5 mg to about 400 mg/kg of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protected delivery formulation) so as to provide therapeutic and/or prophylactic dosage amounts over an extended period. Unit dosage forms in accordance with this invention can have anywhere from less than 1 mg to 500 g of active compound per unit.

Although the anthelmintic agents of this invention will find their primary use in the treatment and/or prevention of helminth parasitisms in domesticated animals such as sheep, cattle, horses, dogs, swine, goats and poultry, they are also effective in treatment that occurs in other warm blooded animals including man. The optimum amount to be employed for best results will, of course, depend upon the particular pyridinyl compound employed, species of animal to be treated, the regimen treatment and the type and severity of helminth infection. Generally good results are obtained with compounds of Formula I by the oral or perenteral route of administration of about 1 to 200 mg/kg of animal bodyweight (such total dose being given at one time, in a protracted manner or in divided doses over a short period of time such as 1-4 days). The technique for administering these materials to animals are known to those skilled in the veterinary and medical fields.

It is contemplated that the pyridinyl acylhydrazones of Formula I can be used to treat various helminth diseases in humans, including those caused by Ascaris, Enterobius, Ancylostoma, Trichuris, Strongyloides, Fasciola, Taenia, and/or Onchocerca or other filaria at a dose of from 1 mg/kg to 200 mg/kg of body weight upon oral and/or parenteral administration.

DEFINITIONS

The definitions and explanations below are for the terms as used throughout the entire patent application including both the specification and claims.

All temperatures are in degrees Celsius.

TLC refers to thin-layer chromatography.

Brine refers to an aqueous saturated sodium chloride solution.

When solvent pairs are used, the ration of solvents used are volume/volume (v/v).

Alkyl of __ to __ carbon atoms, inclusive is used, it means and includes isomers thereof where such exist.

Halogen atom refers to a bromo, chloro, iodo or fluoro atom.

Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.

TABLE A

| C | a | n | $R_1$ | $R_2$ | $R_3$ | $R_4$ | X | | m.p. | P | H |
|---|---|---|---|---|---|---|---|---|---|---|---|
| 1 | 2 | 0 | H | H | $CH_3$ | H | Ph | | 151.6 | 1 | — |
| 2 | 3 | 0 | H | H | $CH_3$ | H | Ph | | 163.9 | 1 | — |
| 3 | 4 | 0 | H | H | $CH_3$ | H | Ph | | 174.5 | 1 | — |
| 4 | 2 | 0 | H | H | H | H | 4-$CH_3$Ph | | 155.3 | 1 | + |
| 5 | 3 | 0 | H | H | $CH_3$ | H | 4-$CH_3$Ph | | 164.8 | 1 | — |
| 6 | 3 | 0 | H | H | H | H | Ph | | 188.4 | 1 | — |
| 7 | 4 | 0 | H | H | H | H | Ph | | 205.3 | 1 | — |
| 8 | 4 | 0 | H | H | Ph | H | Ph | | 114.4 | 1 | + |
| 9 | 2 | 0 | H | H | H | H | Ph | | 86.4 | 1 | + |
| 10 | 4 | 0 | H | H | $CH_3$ | H | 2-$CH_3$Ph | | 187.4 | 2 | — |
| 11 | 4 | 0 | H | H | $CH_3$ | H | 3-$CH_3$Ph | | 146.3 | 2 | — |
| 12 | 4 | 0 | H | H | $CH_3$ | H | 2-$CH_3$OPh | | 152.0 | 2 | — |
| 13 | 4 | 0 | H | H | $CH_3$ | H | 4-$CH_3$OPh | | 171.4 | 2 | — |
| 14 | 4 | 0 | H | H | $CH_3$ | H | 2-$CH_3CH_2$OPh | | 163.5 | 2 | — |
| 15 | 4 | 0 | H | H | $CH_3$ | H | 3-$CH_3CH_2$OPh | | 137.4 | 2 | — |
| 16 | 4 | 0 | H | H | $CH_3$ | H | 4-$CH_3CH_2$OPh | | 185.6 | 2 | — |
| 17 | 4 | 0 | H | H | $CH_3$ | H | 3,4,5-$(CH_3O)_3$Ph | | 198.4 | 2 | — |
| 18 | 4 | 0 | H | H | $CH_3$ | H | 3,4-$(CH_3O)_2$Ph | | 181.7 | 2 | — |
| 19 | 4 | 0 | H | H | H | H | 3,4-$(OCH_2O)$Ph | | 214.6 | 2 | — |
| 20 | 4 | 0 | H | H | $CH_3$ | H | 2-PhO-Ph | | 134.8 | 2 | — |
| 21 | 4 | 0 | H | H | H | H | 2-$CH_3$Ph | | 186.2 | 2 | — |
| 22 | 4 | 0 | H | H | $CH_3$ | H | 3-$CH_3$OPh | | 155.3 | 2 | — |
| 23 | 4 | 0 | H | H | $CH_3$ | H | 3,5-$(CH_3O)_2$Ph | | 190.7 | 2 | — |
| 24 | 4 | 0 | H | H | $CH_3$ | H | 2-ClPh | | 158.3 | 2 | — |
| 25 | 4 | 0 | H | H | $CH_3$ | H | 4-$CH_3$Ph | (2 crops) | 189.1 190.6 | 2 | — |
| 26 | 4 | 0 | H | H | $CH_3$ | H | 2,4-$(Cl)_2$Ph | | 189.1 | 2 | — |
| 27 | 4 | 0 | H | H | $CH_3$ | H | 3,4-$(Cl)_2$Ph | | 223.2 | 2 | — |
| 28 | 4 | 0 | H | H | H | H | 2,4-$(Cl)_2$Ph | | 193.7 | 2 | — |
| 29 | 4 | 0 | H | H | H | H | 3,4-$(Cl)_2$Ph | | 164.3 | 2 | + |
| 30 | 4 | 0 | H | H | H | H | 2-$CH_3$OPh | | 110.5 | 2 | + |
| 31 | 4 | 0 | H | H | H | H | 3-$CH_3$OPh | | 164.0 | 2 | — |
| 31A | 4 | 0 | H | H | H | H | 3-$CH_3$Ph | | 175.7 | 2 | — |
| 32 | 4 | 0 | H | H | H | H | 4-$CH_3$OPh | | 180.2 | 2 | — |
| 33 | 4 | 0 | H | H | H | H | 4-$CH_3$Ph | | 186.5 | 2 | — |
| 34 | 4 | 0 | H | H | H | H | 4-$CH_3CH_2$OPh | | 207.6 | 2 | — |
| 35 | 4 | 0 | H | H | H | H | 3,5-$(CH_3O)_2$Ph | | 185.2 | 2 | — |
| 36 | 4 | 0 | H | H | H | H | 2-ClPh | | 119.9 | 2 | — |
| 37 | 4 | 0 | H | H | H | H | 4-t-$C_4H_9$Ph | | 195.0 | 2 | — |
| 38 | 2 | 0 | H | H | $CH_3$ | H | 4-t-$C_4H_9$Ph | | 148.3 | 2 | — |
| 39 | 4 | 0 | H | H | $CH_3$ | H | 4-t-$C_4H_9$Ph | | 194.7 | 2 | — |
| 40 | 2 | 0 | H | H | H | H | 4-t-$C_4H_9$Ph | | 200.1 | 2 | + |
| 41 | 3 | 0 | H | H | H | H | 4-t-$C_4H_9$Ph | | 138.1 | 2 | + |
| 42 | 3 | 0 | H | H | $CH_3$ | H | 4-t-$C_4H_9$Ph | | 169.6 | 2 | — |
| 43 | 2 | 0 | H | H | H | H | 2-PhOPh | | 169.4 | 2 | — |
| 44 | 4 | 0 | H | H | H | H | 2-$CH_3CH_2$OPh | | 100.4 | 2 | — |
| 45 | 2 | 0 | H | H | $CH_3CH_2$ | H | 2-$CH_3CH_2$OPh | | 137.3 | 2 | — |
| 46 | 3 | 0 | H | H | $CH_3CH_2$ | H | 2-$CH_3CH_2$OPh | | 115.6 | 2 | — |
| 47 | 4 | 0 | H | H | $CH_3CH_2CH_2$ | H | 2-$CH_3CH_2$OPh | | 120.5 | 2 | — |
| 47A | 4 | 1 | H | H | $CH_3CH_2CH_2$ | H | 2-$CH_3CH_2$OPh | | 156.3 | 2 | — |
| 48 | 4 | 1 | H | H | $CH_3$ | H | Ph | | 248.9 | 3 | — |
| 48A | 4 | 1 | H | H | H | H | 4-$CF_3$Ph | | 270.7 | 3 | — |
| 49 | 4 | 1 | H | H | $CH_3$ | H | 2-PhOPh | | 227.2 | 3 | — |
| 50 | 4 | 0 | H | H | $CH_3CH_2CH_2$ | H | 2-PhOPh | | 116.1 | 2 | — |
| 51 | 4 | 0 | H | H | $CH_3CH_2$ | H | Ph | | 177.6 | 4 | — |

TABLE A-continued

| C | a | n | R₁ | R₂ | R₃ | R₄ | X | | m.p. | P | H |
|---|---|---|----|----|----|----|---|---|------|---|---|
| 52 | 4 | 0 | H | H | CH₃CH₂ | H | 4-ClPh | | 170.5 | 4 | — |
| 53 | 4 | 0 | H | H | CH₃CH₂ | H | 3,4-(CH₃O)₂Ph | | 182.0 | 4 | — |
| 54 | 4 | 0 | H | H | i-C₄H₉ | H | 2-PhOPh | | 137.6 | 5 | — |
| 55 | 4 | 0 | H | H | CH₃ | CH₃ | Ph | | 128.3 | 6 | — |
| 56 | 4 | 1 | H | H | CH₃ | H | 2-CH₃OPh | | 248.3 | 3 | — |
| 57 | 2 | 0 | 6-CH₃ | H | H | H | 2-CH₃OPh | | glass | 2 | — |
| 58 | 3 | 0 | H | H | CH₃CH₂ | H | Ph | | 169.4 | 7 | — |
| 59 | 3 | 0 | H | H | CH₃CH₂ | H | 4-ClPh | | 176.1 | 7 | — |
| 60 | 4 | 0 | H | H | n-C₄H₉ | H | Ph | | 142.1 | 8 | — |
| 61 | 4 | 0 | H | H | PhCH₂ | H | Ph | (2 crops) | 84.4 / 90.9 | 10 | — |
| 62 | 4 | 1 | H | H | CH₃ | H | 2,4-(Cl)₂Ph | | 269.4 | 3 | — |
| 63 | 3 | 0 | H | H | H | H | 2,4-(Cl)₂Ph | | 196.0 | 3 | — |
| 64 | 3 | 0 | H | H | CH₃ | H | 2,4-(Cl)₂Ph | | 175.1 | 3 | — |
| 65 | 4 | 0 | H | H | i-C₄H₉ | H | 2-CH₃OPh | | 130.4 | 9 | — |
| 66 | 4 | 0 | H | H | n-C₄H₉ | H | 2,4(Cl)₂Ph | | 185.7 | 3 | — |
| 67 | 2 | 0 | 6-CH₃ | H | H | H | Ph | | 150.2 | 1 | — |
| 68 | 4 | 0 | H | H | CH₃ | H | 2-NO₂Ph | | 150.5 | 2 | — |
| 69 | 4 | 0 | H | H | H | H | 2-NO₂Ph | | 201.1 | 2 | — |
| 70 | 2 | 0 | H | H | CH₃ | H | CH₃CH₂O | | 113.2 | 11 | — |
| 71 | 3 | 0 | H | H | CH₃ | H | CH₃CH₂O | | 116.9 | 11 | — |
| 72 | 4 | 0 | H | H | CH₃ | H | CH₃CH₂O | | 176.5 | 11 | — |
| 73 | 2 | 0 | H | H | H | H | CH₃CH₂O | | 128.9 | 11 | — |
| 74 | 3 | 0 | H | H | H | H | CH₃CH₂O | | 158.4 | 11 | — |
| 75 | 4 | 0 | H | H | H | H | CH₃CH₂O | | 176.1 | 11 | — |
| 76 | 4 | 0 | H | H | CH₃ | H | t-C₄H₉O | | 148.3 | 11 | — |
| 77 | 2 | 0 | H | H | PhCH₂ | H | PhCH₂O | (2 exp.) | 155.1 / 158.7 | 12 | — |
| 78 | 2 | 0 | H | H | CH₃ | H | PhCH₂O | | 155.1 | 12 | — |
| 79 | 4 | 0 | H | H | CH₃ | H | PhCH₂O | | 151.7 | 12 | — |
| 80 | 4 | 0 | H | H | CH₃ | H | Ph₂CHO | (2 exp.) | 172.9 / 179.5 | 12 | — |
| 80A | 2 | 0 | H | H | CH₃ | H | Ph₂CHO | | 210.1 | 12 | — |
| 81 | 4 | 0 | H | H | Ph | H | t-C₄H₉O | | 134.5 | 13 | — |
| 82 | 4 | 0 | H | H | Ph | H | PhCH₂O | | 124.3 | 13 | — |
| 83 | 4 | 0 | H | H | H | H | CH₃O | | 159.6 | 14 | + |
| 84 | 4 | 0 | H | H | H | H | PhCH₂O | | 133.8 | 15 | — |
| 85 | 4 | 0 | H | H | CH₃ | H | CH₃O | | 178.4 | 15 | — |
| 86 | 4 | 0 | H | H | H | H | Ph₂CHO | (2 exp.) | 159–160 / 158–159 | 16 | — |
| 86A | 4 | 1 | H | H | H | H | 4-ClPh | | 244.2 | 16 | — |
| 87 | 4 | 0 | H | H | H | H | Ph₂CHO | | 96.9 | 17 | + |
| 88 | 2 | 0 | H | H | CH₃ | H | CH₃O | | 137.3 | 15 | — |
| 89 | 3 | 0 | H | H | CH₃ | H | CH₃O | | 141.4 | 15 | — |
| 90 | 4 | 0 | H | H | CH₃CH₂ | H | CH₃CH₂O | | 147.1 | 15 | — |
| 91 | 4 | 0 | H | H | CH₃CH₂ | H | t-C₄H₉O | | 170.1 | 19 | — |
| 92 | 4 | 0 | H | H | CH₃CH₂ | H | PhCH₂O | | 134.8 | 3 | — |
| 93 | 4 | 0 | H | H | CH₃CH₂ | H | CH₃O | | 216.2 | 20 | — |
| 94 | 4 | 0 | H | H | CH₃ | H | PhO | | 120.4 | 21 | — |
| 95 | 4 | 0 | H | H | CH₃ | H | PhO.HCl | | 159.1 | 22 | — |
| 96 | 4 | 0 | H | H | Ph | H | CH₃CH₂O | | 188.7 | 23 | — |
| 97 | 4 | 0 | H | H | CH₃ | H | l-menthyl-O | | 188.2 | 24 | — |
| 98 | 4 | 0 | H | H | n-C₄H₉ | H | t-C₄H₉O | | 156.2 | 25 | — |
| 99 | 4 | 0 | H | H | n-C₄H₉ | H | CH₃CH₂O | | 102.1 | 26 | — |
| 100 | 4 | 0 | H | H | CH₃CH₂CH₂ | H | PhO.HCl | | 203.3 | 22 | — |
| 101 | 4 | 0 | H | H | H | H | PhO.HCl | | 224.4 | 27 | — |
| 102 | 4 | 0 | H | H | H | H | l-menthyl-O | | 131.4 | 18 | — |
| 103 | 3 | 0 | H | H | CH₃CH₂ | H | t-C₄H₉O | | 176.6 | 18 | — |
| 104 | 2 | 0 | H | H | CH₃CH₂ | H | CH₃O | | 145.1 | 18 | — |
| 105 | 2 | 0 | H | H | CH₃CH₂ | H | CH₃CH₂O | | 131.0 | 18 | — |
| 106 | 2 | 0 | H | H | CH₃CH₂ | H | t-C₄H₉O | | 184.4 | 18 | — |
| 107 | 3 | 0 | H | H | CH₃CH₂ | H | CH₃CH₂O | | 115.8 | 18 | — |
| 108 | 4 | 0 | H | H | CH₃CH₂CH₂ | H | t-C₄H₉O | | 169.4 | 18 | — |
| 109 | 4 | 1 | H | H | CH₃ | H | CH₃CH₂O | | 220.1 | 28 | — |
| 110 | 4 | 0 | H | H | CH₃CH₂CH₂ | H | CH₃CH₂O | | 127.9 | 20 | — |
| 111 | 4 | 1 | H | H | CH₃ | H | CH₃O | | 228.4 | 22 | — |
| 112 | 4 | 1 | H | H | CH₃CH₂CH₂ | H | PhO | | 206.5 | 29 | — |
| 113 | 4 | 1 | H | H | CH₃CH₂CH₂ | H | t-C₄H₉O | | 186.2 | 29 | — |
| 114 | 4 | 1 | H | H | CH₃CH₂CH₂ | H | CH₃CH₂O | | 196.6 | 29 | — |
| 115 | 4 | 0 | H | H | i-C₄H₉ | H | PhO.HCl | | 200.5 | 29 | — |
| 116 | 4 | 0 | H | H | i-C₄H₉ | H | t-C₄H₉O | | 163.4 | 29 | — |
| 117 | 4 | 0 | H | H | i-C₄H₉ | H | l-menthyl-O | | 143.4 | 29 | — |
| 118 | 4 | 1 | H | H | CH₃ | H | PhO.HCl | | 196.8 | 30 | — |
| 119 | 4 | 1 | H | H | CH₃ | H | PhCH₂O | | 219.4 | 31 | + |
| 120 | 4 | 1 | H | H | CH₃ | H | t-C₄H₉O | | 214.3 | 32 | — |
| 121 | 4 | 0 | H | H | CH₃ | H | 4-CF₃Ph | | 198.4 | 33 | — |
| 122 | 2 | 0 | H | H | H | H | 4-(CH₃)₂NPh | | 223.9 | 33 | — |
| 123 | 3 | 0 | H | H | H | H | 4-(CH₃)₂NPh | | 250.8 | 33 | — |
| 124 | 4 | 0 | H | H | H | H | 4-(CH₃)₂NPh | | 239.8 | 33 | — |
| 125 | 3 | 0 | H | H | CH₃ | H | 4-(CH₃)₂NPh | | 168.4 | 33 | — |
| 126 | 4 | 0 | H | H | CH₃ | H | 4-(CH₃)₂NPh | | 233.0 | 33 | — |

TABLE A-continued

| C | a | n | $R_1$ | $R_2$ | $R_3$ | $R_4$ | X | m.p. | P | H |
|---|---|---|---|---|---|---|---|---|---|---|
| 127 | 3 | 0 | H | H | $CH_3$ | H | 4-$CF_3$Ph | 203.5 | 33 | — |
| 128 | 3 | 0 | H | H | H | H | 4-$CH_3$OPh$CH_2$O | 156.9 | 33 | — |
| 129 | 4 | 0 | H | H | H | H | 4-$CH_3$OPh$CH_2$O | 164.3 | 33 | — |
| 130 | 3 | 0 | H | H | $CH_3$ | H | 4-$CH_3$OPh$CH_2$O | 138.7 | 33 | + |
| 131 | 4 | 0 | H | H | $CH_3$ | H | 4-$CH_3$OPh$CH_2$O | 157.6 | 33 | — |
| 132 | 2 | 0 | 6-$CH_3$ | H | H | H | $CH_3CH_2$O | 102.8 | 2 | + |
| 133 | 2 | 0 | H | H | H | H | 4-$CH_3$OPh$CH_2$O | 121.3 | 2 | — |
| 134 | 3 | 0 | H | H | $CH_3CH_2$ | H | Ph$CH_2$O | 99.7 | 2 | — |
| 135 | 4 | 0 | H | H | i-$C_4H_9$ | H | $CH_3CH_2$O | 99.0 | 2 | — |
| 136 | 4 | 0 | H | H | $CH_3$ | H | $CH_3$ | 177.5–178.5 | 34 | — |
| 137 | 4 | 0 | H | H | $CH_3$ | H | 2,4,5-$(Cl)_3$PhO$CH_2$ | 227.4 | 35 | — |
| 138 | 2 | 0 | 6-$CH_3$ | H | H | H | H | 158.5 | 34 | — |
| 139 | 2 | 0 | H | H | $CH_3$ | H | H | 169.9 | 34 | — |
| 140 | 3 | 0 | H | H | $CH_3$ | H | H | 165.6 | 34 | — |
| 141 | 4 | 0 | H | H | n-$C_4H_9$ | H | H | 143.4 | 37 | — |
| 142 | 2 | 0 | 6-$CH_3$ | H | H | H | Ph$CH_2$ | 96.6 | 34 | — |
| 143 | 2 | 0 | H | H | $CH_3$ | H | $CH_3CH_2CH_2$ | 123.5 | 34 | — |
| 144 | 4 | 0 | H | H | $CH_3$ | H | $CH_3CH_2CH_2$ | 131.8 | 34 | — |
| 145 | 4 | 0 | H | H | $CH_3$ | H | $CH_3CH_2CH_2.(CO_2H)_2$ | 207.2 | 38 | — |
| 146 | 4 | 0 | H | H | $CH_3$ | H | $CH_3CH_2CH_2$.panoic acid salt | 291.5 | 38 | — |
| 147 | 4 | 0 | H | H | $CH_3$ | H | $CH_3CH_2CH_2$.1-OH-2-naphthoic acid salt | 158.7 | 39 | — |
| 148 | 4 | 0 | H | H | $CH_3$ | H | $CH_3CH_2CH_2$.3-OH-2-naphthoic acid salt | 149.1 | 39 | — |
| 149 | 4 | 0 | H | H | $CH_3$ | H | $CH_3CH_2CH_2.CH_2(CO_2H)_2$ | 140.0 | 39 | — |
| 150 | 4 | 0 | H | H | $CH_3$ | H | $CH_3CH_2CH_2.PhCH_2CO_2H$ | 102.3 | 39 | — |
| 151 | 4 | 0 | H | H | $CH_3$ | H | $CH_3CH_2CH_2.PhOCH_2CO_2H$ | 105.8 | 40 | — |
| 152 | 4 | 0 | H | H | $CH_3$ | H | $CH_3CH_2CH_2.PhSCH_2CO_2H$ | 97.2 | 40 | — |
| 153 | 4 | 0 | H | H | H | H | $CH_3CH_2CH_2$ | 156.6 | 34 | — |
| 154 | 4 | 0 | H | H | H | H | $CH_3CH_2CH_2.(CO_2H)_2$ | 175.4 | 38 | — |
| 155 | 4 | 0 | H | H | $CH_3$ | H | H | 195.7 | 34 | — |
| 156 | 3 | 0 | H | H | $CH_3$ | H | $CH_3CH_2CH_2$ | 106.7 | 34 | — |
| 157 | 4 | 0 | H | H | $CH_3$ | H | Ph$CH_2$ | 148.5 | 34 | — |
| 158 | 4 | 0 | H | H | $CH_3$ | H | 2-Cl-4-$NO_2$Ph | 232.2 | 2 | — |
| 159 | 4 | 0 | H | H | $CH_3$ | H | c-$C_6H_{11}$ | 195.3 | 41 | — |
| 160 | 4 | 1 | H | H | $CH_3$ | H | c-$C_6H_{11}$—$CH_2CH_2$ | 183.1 | 3 | — |
| 161 | 4 | 0 | H | H | $CH_3$ | H | 1-naphthyl | 183.7 | 2 | — |
| 162 | 4 | 0 | H | H | $CH_3$ | H | 2-naphthyl | 206.5 | 2 | — |
| 163 | 4 | 0 | H | H | 4-ClPh | H | $CH_3CH_2$O.HCl | 216.9 | 42 | — |
| 164 | 4 | 0 | H | H | H | H | 1-naphthyl$CH_2$ | 185.2 | 2 | — |
| 165 | 3 | 0 | H | H | $CH_3$ | H | 1-naphthyl$CH_2$ | 159.3 | 2 | — |
| 166 | 4 | 0 | H | H | $CH_3$ | H | 1-naphthyl$CH_2$ | 168.6 | 2 | — |
| 167 | 2 | 0 | 6-$CH_3$ | H | H | H | c-$C_6H_{11}$ | 102.4 | 2 | + |
| 168 | 2 | 0 | 6-$CH_3$ | H | H | H | $CH_3CH_2CH_2$ | 115.1 | 2 | — |
| 169 | 2 | 0 | 6-$CH_3$ | H | H | H | $(CH_3)_2$CH | 99.2 | 2 | — |
| 170 | 4 | 0 | H | H | Ph$CH_2$ | H | $CH_3CH_2CH_2$ | 108.9 | 2 | — |
| 171 | 4 | 1 | H | H | $CH_3$ | H | 1-naphthyl | 251.7 | 2 | — |
| 172 | 3 | 0 | H | H | H | H | 1-naphthyl | (2 crops) 197.1 199.5 | 2 | — |
| 173 | 4 | 0 | H | H | Ph$CH_2$ | H | 1-naphthyl | 187.9 | 2 | — |
| 174 | 3 | 0 | H | H | $CH_3CH_2$ | H | 3-pyridyl | 163.5 | 2 | — |
| 175 | 4 | 0 | H | H | n-$C_4H_9$ | H | 3-pyridyl | 125.6 | 2 | — |
| 176 | 4 | 0 | H | H | n-$C_4H_9$ | H | 2-thienyl | 176.6 | 2 | — |
| 177 | 4 | 0 | H | H | $CH_3$ | H | 2-thienyl | 198.4 | 2 | — |
| 178 | 3 | 0 | H | H | $CH_3$ | H | 2-thienyl | 159.8 | 2 | — |
| 179 | 3 | 0 | H | H | H | H | 2-thienyl | 223.9 | 2 | — |
| 180 | 4 | 0 | H | H | H | H | 1-naphthyl | 199.2 | 2 | — |
| 181 | 4 | 0 | H | H | H | H | 2-thienyl | 200.9 | 2 | — |
| 182 | 4 | 0 | H | H | H | H | 3,4,5-$(CH_3O)_3$Ph | 187.8 | 2 | + |
| 183 | 2 | 0 | 6-$CH_3$ | H | H | H | c-$C_4H_7$ | 120.0 | 2 | — |
| 184 | 2 | 0 | 6-$CH_3$ | H | H | H | $CH_3$ | 156.9 | 2 | — |
| 185 | 3 | 0 | H | H | $CH_3CH_2$ | H | c-$C_4H_7$ | 153.6 | 2 | — |
| 186 | 3 | 0 | H | H | $CH_3CH_2$ | H | 1-naphthyl | 166.7 | 2 | — |
| 187 | 3 | 0 | H | H | $CH_3$ | H | 1-naphthyl | 166.9 | 2 | + |
| 188 | 4 | 0 | H | H | $CH_3$ | H | 4-ClPh | 182.0 | 2 | — |
| 189 | 4 | 1 | H | H | $CH_3$ | H | 4-ClPh | 224.0 | 2 | — |
| 190 | 3 | 0 | H | H | $CH_3$ | H | 4-ClPh | 180.9 | 2 | — |
| 191 | 2 | 0 | 6-$CH_3$ | H | H | H | 4-ClPh | 169.3 | 2 | — |
| 192 | 4 | 0 | H | H | Ph$CH_2$ | H | $CH_3CH_2$O | 131–133 | 2 | — |
| 193 | 4 | 0 | H | H | H | H | 4-ClPh | 170.5 | 2 | — |
| 194 | 3 | 0 | H | H | H | H | 4-ClPh | 233.5 | 2 | — |
| 195 | 2 | 0 | H | H | $CH_3$ | H | 1-naphthyl$CH_2$ | 201.2 | 3 | — |
| 196 | 4 | 0 | H | H | $CH_3CH_2$ | H | $CH_3CH_2CH_2$ | 151.3 | 3 | — |
| 197 | 4 | 0 | H | H | $CH_3CH_2$ | H | Ph$CH_2$ | 147.2 | 3 | — |
| 198 | 4 | 0 | H | H | $CH_3$ | H | 3-pyridyl | 143.7 | 3 | — |
| 199 | 3 | 0 | H | H | $CH_3$ | H | 3-pyridyl | 166.7 | 3 | — |
| 200 | 2 | 0 | H | H | $CH_3$ | H | 3-pyridyl | 178.0 | 3 | — |
| 201 | 4 | 0 | H | H | $CH_3$ | H | chrysanthemyl | 161.9 | 3 | — |
| 202 | 4 | 1 | H | H | $CH_3$ | H | $(CH_3)_3$CH | 251.3 | 3 | — |
| 203 | 4 | 1 | H | H | $CH_3$ | H | H | 236.1 | 3 | — |

TABLE A-continued

| C | a | n | R₁ | R₂ | R₃ | R₄ | X | | m.p. | P | H |
|---|---|---|----|----|----|----|----|----|------|---|---|
| 204 | 2 | 0 | H | H | CH₃CH₂ | H | CH₃ | | 173.1 | 3 | — |
| 205 | 4 | 1 | H | H | CH₃ | H | CH₃ | | 240.7 | 3 | — |
| 206 | 4 | 1 | H | H | CH₃ | H | c-C₃H₅ | | 292.4 | 3 | — |
| 207 | 4 | 1 | H | H | CH₃CH₂CH₂ | H | H | (3 crops) | 221.3 | 3 | — |
| | | | | | | | | | 221.2 | | |
| | | | | | | | | | 215.9 | | |
| 208 | 4 | 1 | H | H | CH₃CH₂CH₂ | H | c-C₃H₅ | | 238.5 | 3 | — |
| 209 | 4 | 1 | H | H | CH₃CH₂CH₂ | H | i-C₃H₇ | | 241.6 | 3 | — |
| 210 | 2 | 0 | H | H | CH₃CH₂ | H | H | | 141.2 | 3 | — |
| 211 | 4 | 1 | H | H | CH₃CH₂CH₂ | H | CH₃CH₂CH₂ | | 199.2 | 3 | — |
| 212 | 4 | 1 | H | H | CH₃CH₂CH₂ | H | CH₃ | | 218.9 | 3 | — |
| 213 | 4 | 1 | H | H | CH₃CH₂CH₂ | H | c-C₆H₁₁ | | 265.9d | 3 | — |
| 214 | 3 | 0 | H | H | CH₃ | H | 2-furyl | | 130.6 | 3 | + |
| 215 | 2 | 0 | H | H | CH₃ | H | 2-furyl | | 123.9 | 3 | — |
| 216 | 2 | 0 | H | H | H | H | 2-furyl | | 154.7 | 3 | — |
| 217 | 4 | 0 | H | H | CH₃ | H | 4-pyridyl | | 174.5 | 3 | — |
| 218 | 3 | 0 | H | H | CH₃ | H | 4-pyridyl | | 174.0 | 3 | — |
| 219 | 2 | 0 | H | H | CH₃ | H | 4-pyridyl | | 166.9 | 3 | — |
| 220 | 4 | 0 | H | H | H | H | 4-pyridyl | | 234.4 | 3 | — |
| 221 | 2 | 0 | H | H | H | H | 4-pyridyl | | 163.4 | 3 | — |
| 222 | 4 | 0 | H | H | CH₃CH₂ | H | 1-naphthyl | | 204.3 | 3 | — |
| 223 | 3 | 0 | H | H | H | H | 1-naphthylCH₂ | | 209.4 | 3 | — |
| 224 | 4 | 0 | H | H | H | H | 3,4,5-(CH₃O)₃Ph | | 188.7 | 3 | — |
| 225 | 3 | 0 | H | H | CH₃ | H | 2-furyl | | 133.1 | 3 | — |
| 226 | 3 | 0 | H | H | CH₃CH₂ | H | PhO.HCl | | 155.3 | 3 | — |
| 227 | 4 | 1 | H | H | CH₃ | H | c-C₄H₇ | | 232.3 | 3 | + |
| 228 | 4 | 1 | H | H | CH₃ | H | CH₃CH₂OCH₂CH₂ | | 202.1 | 3 | — |
| 229 | 4 | 1 | H | H | H | H | 2-CH₃OPh | | 216.1 | 3 | — |
| 230 | 4 | 1 | H | H | H | H | PhO.HCl | | 187.0 | 3 | — |
| 231 | 4 | 1 | H | H | H | H | H | | 290.4d | 3 | — |
| 232 | 4 | 1 | H | H | H | H | 3-pyridyl | | 255.6d | 3 | — |
| 233 | 4 | 1 | H | H | H | H | CH₃CH₂O | | 252.9d | 3 | — |
| 234 | 4 | 1 | H | H | H | H | Ph | | 234.1 | 3 | — |
| 235 | 4 | 1 | H | H | H | H | CH₃CH₂CH₂ | | 250.8d | 3 | — |
| 236 | 4 | 1 | H | H | H | H | 2-PhOPh | | 186.7 | 3 | — |
| 237 | 4 | 1 | H | H | H | H | i-C₃H₇ | | 238.5 | 3 | — |
| 238 | 4 | 1 | H | H | H | H | i-C₆H₁₁ | | 266.6 | 3 | — |
| 239 | 4 | 1 | H | H | H | H | 2-thienyl | | 262.4d | 3 | — |
| 240 | 4 | 1 | H | H | H | H | 4-pyridyl | | 273.1d | 3 | — |
| 241 | 4 | 1 | H | H | H | H | c-C₆H₁₁—CH₂CH₂ | | 193.4 | 3 | — |
| 242 | 4 | 0 | H | H | CH₃CH₂CH₂ | H | CH₃CH₂CH₂ | | 112.8 | 9 | — |
| 243 | 4 | 0 | H | H | i-C₄H₉ | H | c-C₆H₁₁—CH₂CH₂ | | 166.2 | 9 | — |
| 244 | 4 | 0 | H | H | i-C₄H₉ | H | c-C₃H₅ | | 210.8 | 9 | — |
| 245 | 4 | 0 | H | H | i-C₄H₉ | H | c-C₆H₁₁—CH₂ | | 141.3 | 9 | — |
| 246 | 4 | 0 | H | H | c-C₅H₉ | H | c-C₆H₁₁ | | 163.0 | 9 | — |
| 247 | 4 | 0 | H | H | c-C₅H₉ | H | CH₃CH₂CH₂ | | 98.1 | 9 | — |
| 248 | 4 | 0 | H | H | CH₃CH₂CH₂ | H | c-C₃H₅ | | 181.7 | 9 | — |
| 249 | 4 | 0 | H | H | CH₃CH₂CH₂ | H | (CH₃)₂CH | | 165.4 | 9 | — |
| 250 | 4 | 0 | H | H | CH₃CH₂CH₂ | H | c-C₆H₁₁—CH₂CH₂ | | 154.6 | 9 | — |
| 251 | 2 | 0 | H | Ph | H | H | 2-furyl | | 139.6 | 9 | — |
| 252 | 4 | 0 | H | H | CH₃CH₂CH₂ | H | c-C₆H₁₁—CH₂ | | 151.4 | 9 | — |
| 253 | 4 | 0 | H | H | CH₃CH₂CH₂ | H | c-C₆H₁₁ | | 184.1 | 9 | — |
| 254 | 4 | 0 | H | H | i-C₄H₉ | H | (CH₃)₂CH | | 146.3 | 9 | — |
| 255 | 4 | 0 | H | H | i-C₄H₉ | H | c-C₆H₁₁ | | 178.2 | 9 | — |
| 256 | 4 | 0 | H | H | i-C₄H₉ | H | CH₃CH₂CH₂ | | 106.0 | 9 | — |
| 257 | 4 | 0 | H | H | i-C₄H₉ | H | 2-CH₃CH₂OPh | | 108.4 | 9 | — |
| 258 | 3 | 0 | H | H | CH₃ | H | c-C₆H₁₁—CH₂ | | 117.2 | 24 | — |
| 259 | 2 | 0 | H | H | CH₃ | H | c-C₆H₁₁—CH₂ | | 116.3 | 24 | — |
| 260 | 2 | 0 | H | H | CH₃ | H | CH₃CH₂OCH₂CH₂ | | 98.3 | 24 | — |
| 261 | 3 | 0 | H | H | H | H | CH₃CH₂OCH₂CH₂ | | 99.0 | 24 | — |
| 262 | 4 | 0 | H | H | CH₃ | H | CH₃CH₂OCH₂CH₂ | | 116.7 | 24 | — |
| 263 | 4 | 0 | H | H | CH₃CH₂CH₂ | H | H | | 147.4 | 41 | — |
| 264 | 4 | 0 | H | H | H | H | c-C₄H₇ | | 178.1 | 41 | — |
| 265 | 4 | 0 | H | H | CH₃ | H | 3-[(1-CH₃)-c-C₅H₉N] | | 142.8 | 41 | — |
| 266 | 4 | 0 | H | H | CH₃ | H | 2-[(1-CH₃)-c-C₅H₉N] | | 140.1 | 41 | — |
| 267 | 3 | 0 | H | H | CH₃ | H | 2-[(1-CH₃)-c-C₅H₉N] | | 102.5 | 41 | + |
| 268 | 3 | 0 | H | H | CH₃ | H | 3-[(1-CH₃)-c-C₅H₉N] | | 121.5 | 41 | + |
| 269 | 2 | 0 | H | H | CH₃ | H | c-C₆H₁₁ | | 147.3 | 41 | — |
| 270 | 4 | 0 | H | H | H | H | c-C₆H₁₁ | | 159.8 | 41 | — |
| 271 | 3 | 0 | H | H | CH₃CH₂ | H | H | | 128.7 | 41 | — |
| 272 | 4 | 0 | H | H | H | H | (CH₃)₂CH | | 154.9 | 41 | — |
| 273 | 4 | 0 | H | H | CH₃ | H | c-C₃H₅ | | 197.7 | 41 | — |
| 274 | 4 | 0 | H | H | H | H | c-C₃H₅ | | 191.6 | 41 | — |
| 275 | 4 | 0 | H | H | CH₃ | H | (CH₃)₂CH | | 149.2 | 41 | — |
| 276 | 4 | 0 | H | H | CH₃ | H | c-C₆H₁₁—CH₂CH₂ | | 139.2 | 41 | — |
| 277 | 4 | 0 | H | H | H | H | c-C₆H₁₁—CH₂CH₂ | | 131.2 | 41 | — |
| 278 | 4 | 0 | H | H | H | H | c-C₆H₁₁—CH₂ | | 114.4 | 41 | — |
| 279 | 3 | 0 | H | H | CH₃ | H | c-C₆H₁₁ | | 172.3 | 41 | — |
| 280 | 4 | 0 | H | H | CH₃ | H | c-C₆H₁₁—CH₂ | | 159.3 | 41 | " |
| 281 | 4 | 0 | H | H | CH₃CH₂ | H | CH₃CH₂OCH₂CH₂ | | 123.1 | 41 | — |
| 282 | 4 | 0 | H | H | CH₃CH₂ | H | c-C₄H₇ | | 177.5 | 41 | — |

TABLE A-continued

| C | a | n | $R_1$ | $R_2$ | $R_3$ | $R_4$ | X | m.p. | P | H |
|---|---|---|---|---|---|---|---|---|---|---|
| 283 | 4 | 0 | H | H | H | H | $CH_3CH_2OCH_2CH_2$ | 92.3 | 41 | — |
| 284 | 4 | 0 | H | H | Ph | H | 2-$CH_3$OPh.HCl | 242.1 | 42 | — |
| 285 | 4 | 0 | H | H | Ph | H | 2-PhOPh.HCl | 249.8 | 42 | — |
| 286 | 4 | 0 | H | H | Ph | H | PhO.HCl | 217.0d | 42 | — |
| 287 | 4 | 1 | H | H | $CH_3$ | H | c-$C_6H_{11}$ | 245.3 | 43 | — |
| 288 | 4 | 1 | H | H | $CH_3$ | H | c-$C_6H_{11}$—$CH_2$ | 214.7 | 43 | — |
| 289 | 4 | 1 | H | H | $CH_3$ | H | $CH_3CH_2CH_2$ | 209.7 | 44 | + |
| 290 | 4 | 0 | H | H | $CH_3$ | H | c-$C_4H_7$ | 138.6 | 45 | — |
| 291 | 4 | 0 | H | H | $CH_3$ | H | 4-$NO_2$Ph | 251.2 | 46 | — |
| 292 | 4 | 0 | H | H | $CH_3$ | H | 3-$NO_2$Ph | 238.6d | 46 | — |
| 293 | 4 | 0 | H | H | H | H | 2-Cl-4-$NO_2$Ph | 232.9 | 46 | — |
| 294 | 4 | 0 | H | H | H | H | 4-$NO_2$Ph | 300.0 | 46 | — |
| 295 | 4 | 0 | H | H | H | H | 3-$NO_2$Ph | 289.3 | 46 | — |
| 296 | 3 | 0 | H | H | $CH_3CH_2$ | H | $CH_3$ | 123.2 | 24 | — |
| 297 | 3 | 0 | H | H | $CH_3CH_2$ | H | $CH_3O$ | 125.8 | 24 | — |
| 298 | 4 | 1 | H | H. | H | H | 4-$CF_3$Ph | 270.7d | 3 | — |
| 299 | 2 | 0 | H | H | $CH_3$ | H | 4-$CH_3$OPh$CH_2$—O | 121.6 | 2 | — |
| 300 | 2 | 0 | H | H | H | H | 1-naphthyl$CH_2$ | 119.2 | 2 | + |
| 301 | 2 | 0 | H | H | $CH_3$ | H | 3-$CF_3$Ph | 183.3 | 50 | — |
| 302 | 3 | 0 | H | H | H | H | 3-$CF_3$Ph | 106–108 | 48 | — |
| 303 | 2 | 0 | H | H | H | H | 2-FPh | 144.9 | 2 | — |
| 304 | 2 | 0 | H | H | $CH_3$ | H | 2-FPh | 132.7 | 2 | — |
| 305 | 2 | 0 | H | H | $CH_3$ | H | 3-FPh | 154.3 | 3 | — |
| 306 | 2 | 0 | H | H | H | H | 3-FPh | 123.6 | 48 | — |
| 307 | 2 | 0 | H | H | H | H | 2-$CH_3$-c-$C_3H_6$ | 112.7 | 47 | — |
| 308 | 3 | 0 | H | H | $CH_3CH_2$ | H | 3,4-($OCH_2O$)Ph | 142.5 | 2 | — |
| 309 | 3 | 0 | H | H | $CH_3CH_2$ | H | 3,4-($CH_3O)_2$Ph$CH_2$ | 140.0 | 2 | — |
| 310 | 3 | 0 | H | H | $CH_3CH_2$ | H | $CH_3CH_2$ | 147.1 | 7 | — |
| 311 | 3 | 0 | H | H | $CH_3$ | H | $CH_3CH_2$ | 138.8 | 2 | — |
| 312 | 3 | 0 | H | H | $CH_3$ | H | 1-$CH_3$-c-$C_3H_5$ | 104.4 | 47 | — |
| 313 | 3 | 0 | H | H | $CH_3CH_2$ | H | 2-$CH_3$-c-$C_3H_5$ | 137.3 | 47 | — |
| 314 | 3 | 0 | H | H | H | H | 2-$CH_3$-c-$C_3H_5$ | 101.7 | 47 | — |
| 315 | 3 | 0 | H | H | H | H | 3-$CF_3$Ph | 153.6 | 2 | — |
| 316 | 3 | 0 | H | H | $CH_3CH_2$ | H | 3-$CF_3$Ph | 119.4 | 48 | — |
| 317 | 3 | 0 | H | H | $CH_3$ | H | 3-$CF_3$Ph | 157.2 | 48 | — |
| 318 | 3 | 0 | H | H | $CH_3CH_2$ | H | 2-FPh | 122.3 | 2 | — |
| 319 | 3 | 0 | H | H | $CH_3CH_2$ | H | 3-FPh | 156.9 | 48 | — |
| 320 | 3 | 0 | H | H | H | H | 2-FPh | 187.7 | 2 | — |
| 321 | 3 | 0 | H | H | $CH_3$ | H | 2-FPh | 134.6 | 2 | — |
| 322 | 3 | 0 | H | H | H | H | 3-FPh | 192.2 | 48 | — |
| 323 | 3 | 0 | H | H | $CH_3$ | H | 3-FPh | 166.6 | 48 | — |
| 324 | 3 | 0 | H | H | $CH_3CH_2$ | H | $PhCH_2CH_2CH_2$ | 93.7 | 2 | — |
| 325 | 3 | 0 | H | H | H | H | $PhCH_2CH_2CH_2$ | 116.5 | 2 | — |
| 326 | 3 | 0 | 6-$CH_3$ | H | $CH_3$ | H | H | 175.1 | 2 | — |
| 327 | 3 | 0 | 6-$CH_3$ | H | $CH_3$ | H | $CH_3$ | 178.5 | 49 | — |
| 328 | 3 | 0 | 6-$CH_3$ | H | $CH_3$ | H | i-$C_3H_7$ | 144.8 | 49 | — |
| 329 | 3 | 0 | 6-$CH_3$ | H | $CH_3$ | H | $CH_3CH_2CH_2$ | 145.1 | 2 | — |
| 330 | 3 | 0 | 6-$CH_3$ | H | $CH_3$ | H | $CH_3CH_2$ | 170.4 | 48 | — |
| 331 | 3 | 0 | 6-$CH_3$ | H | $CH_3$ | H | $CH_3O$ | 128.6 | 48 | — |
| 332 | 3 | 0 | 6-$CH_3$ | H | $CH_3$ | H | $CH_3CH_2O$ | 121.0 | 2 | — |
| 333 | 3 | 0 | 6-$CH_3$ | H | $CH_3$ | H | t-$C_4H_9O$ | 164.7 | 48 | — |
| 334 | 3 | 0 | 6-$CH_3$ | H | $CH_3$ | H | PhO.HCl | 209.6 | 7 | — |
| 335 | 3 | 0 | 6-$CH_3$ | H | $CH_3$ | H | 1-menthyl-O | 153.5 | 48 | — |
| 336 | 3 | 0 | 6-$CH_3$ | H | $CH_3$ | H | Ph | 161.2 | 48 | — |
| 337 | 3 | 0 | 6-$CH_3$ | H | $CH_3$ | H | 4-ClPh | 207.6 | 2 | — |
| 338 | 3 | 0 | 6-$CH_3$ | H | $CH_3$ | H | 2-$CH_3CH_2$OPh | 146.5 | 48 | — |
| 339 | 3 | 0 | 6-$CH_3$ | H | $CH_3$ | H | 4-$CH_3CH_2$OPh | 184.2 | 48 | — |
| 340 | 4 | 0 | H | H | $CH_3$ | H | 2-norbornyl | 191.0 | 2 | — |
| 341 | 4 | 0 | H | H | $CH_3$ | H | 2-$CH_3$-1-naphthyl$CH_2$ | 189.6 | 4 | — |
| 342 | 4 | 0 | H | H | $CH_3$ | H | 3-$NO_2$-1-naphthyl | 228.5 | 51 | — |
| 343 | 4 | 0 | H | H | $CH_3$ | H | 5-$NO_2$-1-naphthyl | 232.0 | 4 | — |
| 344 | 4 | 0 | H | H | $CH_3$ | $CH_3$ | $CH_3$ | 80.7 | 6 | — |
| 345 | 4 | 1 | H | H | H | H | t-$C_4H_9O$ | d>300 | 3 | — |
| 346 | 4 | 1 | H | H | $CH_3$ | H | 3,4-($OCH_2O$)Ph | 266.3d | 2 | + |
| 347 | 4 | 0 | H | H | $CH_3$ | H | 3,4-($OCH_2O$)Ph | 200.0 | 2 | — |
| 348 | 4 | 1 | H | H | $CH_3$ | H | 3,4-($CH_3O)_2$Ph$CH_2$ | 242.9 | 2 | + |
| 349 | 4 | 0 | H | H | H | H | 3,4-($CH_3O)_2$Ph$CH_2$ | 138.0 | 2 | — |
| 350 | 4 | 0 | H | H | $CH_3$ | H | 3,4-($CH_3O)_2$Ph$CH_2$ | 145.5 | 2 | — |
| 351 | 4 | 0 | H | H | H | H | $CH_3CH_2$ | 132.5 | 2 | — |
| 352 | 4 | 0 | H | H | $CH_3$ | H | $CH_3CH_2$ | 150.0 | 2 | — |
| 353 | 4 | 0 | H | H | Ph | H | 3-pyridyl | 74.0 | 52 | — |
| 354 | 4 | 0 | H | H | $CH_3$ | H | 1-$CH_3$-c-$C_3H_5$ | 122.0 | 47 | — |
| 355 | 4 | 0 | H | H | H | H | 1-$CH_3$-c-$C_3H_5$ | 192.0 | 49 | — |
| 356 | 4 | 0 | H | H | $CH_3$ | H | 2-$CH_3$-c-$C_3H_5$ | 165.4 | 2 | — |
| 357 | 4 | 0 | H | H | H | H | 2-$CH_3$-c-$C_3H_5$ | 186.3 | 49 | — |
| 358 | 4 | 0 | H | H | H | H | 3-$CF_3$Ph | 128.8 | 2 | — |
| 359 | 4 | 0 | H | H | $CH_3$ | H | 3-$CF_3$Ph | 173.0 | 48 | — |
| 360 | 4 | 0 | H | H | $CH_3CH_2$ | H | 2-$CH_3$-c-$C_3H_5$ | 192.1 | 2 | — |
| 361 | 4 | 0 | H | H | $CH_3CH_2$ | H | 3-$CF_3$Ph | 130.8 | 2 | — |
| 362 | 4 | 0 | H | H | $CH_3CH_2$ | H | 2-FPh | 122.3 | 2 | — |
| 363 | 4 | 0 | H | H | $CH_3CH_2$ | H | 3-FPh | 176.2 | 2 | — |

TABLE A-continued

| C | a | n | R₁ | R₂ | R₃ | R₄ | X | m.p. | P | H |
|---|---|---|----|----|----|----|----|------|---|---|
| 364 | 4 | 0 | H | H | H | H | 2-FPh | 164.3 | 2 | — |
| 365 | 4 | 0 | H | H | CH₃ | H | 2-FPh | 167.5 | 3 | — |
| 366 | 4 | 0 | H | H | H | H | 3-FPh | 154.3 | 3 | — |
| 367 | 4 | 0 | H | H | CH₃ | H | 3-PhCH₂CH₂CH₂ | 129.3 | 2 | — |
| 368 | 4 | 0 | H | H | CH₃CH₂ | H | 3-PhCH₂CH₂CH₂ | 129.3 | 2 | — |
| 369 | 4 | 0 | H | H | H | H | 3-PhCH₂CH₂CH₂ | 111.3 | 2 | — |
| 370 | 4 | 0 | H | H | CH₃ | H | 3-FPh | 164.1 | 48 | — |
| 371 | 4 | 0 | H | H | CH₃CH₂ | H | 2-CH₃Ph | 173.3 | 2 | — |
| 372 | 4 | 0 | H | H | CH₃CH₂ | H | 3-CH₃Ph | 169.3 | 2 | — |
| 373 | 4 | 0 | H | H | CH₃CH₂ | H | 4-CH₃Ph | 171.4 | 2 | — |
| 374 | 4 | 0 | H | H | CH₃CH₂ | H | 2-ClPh | 161.5 | 2 | — |
| 375 | 4 | 0 | H | H | CH₃CH₂ | H | 2-NO₂Ph | 214.2 | 3 | — |
| 376 | 4 | 0 | H | H | CH₃ | H | 5-CH₃-2-thienyl | 175.6 | 41 | — |
| 377 | 4 | 0 | H | H | CH₃CH₂ | H | CH₃ | 123.9 | 47 | — |
| 378 | 4 | 0 | H | H | CH₃CH₂ | H | 2-furyl | 125.4 | 47 | — |
| 379 | 4 | 0 | H | H | CH₃CH₂ | H | 4-pyridyl | 193.5 | 47 | — |
| 380 | 4 | 0 | H | H | CH₃CH₂ | H | CH₃CH₂ | 136.2 | 47 | — |
| 381 | 4 | 0 | H | H | CH₃CH₂ | H | i-C₃H₇ | 194.3 | 2 | — |
| 382 | 4 | 0 | H | H | CH₃CH₂ | H | 2-thienyl | 217.9 | 5 | — |
| 383 | 4 | 0 | H | H | CH₃CH₂ | H | PhO.HCl | 196.4 | 47 | — |
| 384 | 4 | 0 | H | H | CH₃CH₂ | H | 1-menthyl-O | 181.7 | 50 | — |
| 385 | 4 | 0 | H | H | CH₃CH₂ | H | 2-CH₃CH₂OPh | 151.7 | 10 | — |
| 386 | 4 | 0 | H | H | CH₃CH₂ | H | H | 120.8 | 47 | — |
| 387 | 4 | 0 | H | H | CH₃CH₂ | H | 4-ClPh | 163.8 | 10 | — |
| 388 | 4 | 0 | H | H | CH₃CH₂ | H | 4-CH₃CH₂OPh | 156.7 | 10 | — |
| 389 | 4 | 0 | H | H | CH₃CH₂ | H | 3-ClPh | 155.6 | 10 | — |
| 390 | 4 | 0 | H | H | CH₃CH₂ | H | 3,4,5-(CH₃O)₃Ph | 174.5 | 10 | — |
| 391 | 3 | 0 | 2-Cl | H | H | H | n-C₃H₇ | 144.7 | 7 | — |
| 392 | 2 | 0 | 3-OH | H | H | H | n-C₃H₇ | 134.7 | 19 | — |
| 393 | 2 | 0 | 3-OH | H | H | H | CH₃CH₂ | 193.5d | 19 | — |
| 394 | 4 | 0 | 3-Cl | H | CH₃ | H | H | 175.2 | 53 | — |
| 395 | 4 | 0 | 3-Cl | H | CH₃ | H | n-C₃H₇ | 103.8 | 54 | — |
| 396 | 4 | 0 | 3-Cl | H | CH₃ | H | CH₃O | 183.6 | 54 | — |
| 397 | 3 | 0 | 2-Cl | H | CH₃ | H | H | 119.1 | 53 | — |
| 398 | 3 | 0 | 2-Cl | H | CH₃ | H | CH₃ | 192.4 | 54 | — |
| 399 | 3 | 0 | 2-Cl | H | CH₃ | H | CH₃CH₂ | 157.5 | 54 | — |
| 400 | 3 | 0 | 2-Cl | H | CH₃ | H | n-C₃H₇ | 155.6 | 54 | — |
| 401 | 3 | 0 | 2-Cl | H | CH₃ | H | i-C₃H₇ | 147.5 | 54 | — |
| 402 | 3 | 0 | 2-Cl | H | CH₃ | H | c-C₃H₅ | 148.2 | 54 | — |
| 403 | 3 | 0 | 2-Cl | H | CH₃ | H | c-C₆H₁₁CH₂ | 119.3 | 53 | — |
| 404 | 3 | 0 | 2-Cl | H | CH₃ | H | Ph | | 53 | |
| 405 | 3 | 0 | 2-Cl | H | CH₃ | H | CH₃O | 191.2 | 54 | — |
| 406 | 3 | 0 | 2-Cl | H | CH₃ | H | PhO.HCl | | 16 | |
| 407 | 3 | 0 | 2-Cl | H | CH₃ | H | 4-CH₃CH₂OPh | | 53 | |
| 408 | 3 | 0 | 2-Cl | H | CH₃ | H | 4-pyridyl | 161.2 | 54 | — |
| 409 | 3 | 0 | 6-Cl | H | CH₃ | H | H | 202.0 | 53 | — |
| 410 | 3 | 0 | 6-Cl | H | CH₃ | H | CH₃ | 191.9 | 54 | — |
| 411 | 3 | 0 | 6-Cl | H | CH₃ | H | CH₃CH₂ | 208.6 | 54 | — |
| 412 | 3 | 0 | 6-Cl | H | CH₃ | H | CH₃CH₂CH₂ | 177.3 | 54 | — |
| 413 | 3 | 0 | 6-Cl | H | CH₃ | H | i-C₃H₇ | 172.7 | 54 | — |
| 414 | 3 | 0 | 6-Cl | H | CH₃ | H | c-C₃H₅ | 214.8d | 55 | — |
| 415 | 3 | 0 | 6-Cl | H | CH₃ | H | c-C₆H₁₁—CH₂ | 172.3 | 54 | — |
| 416 | 3 | 0 | 6-Cl | H | CH₃ | H | Ph | 189.9 | 54 | — |
| 417 | 3 | 0 | 6-Cl | H | CH₃ | H | CH₃O | 177.1 | 54 | — |
| 418 | 3 | 0 | 6-Cl | H | CH₃ | H | PhO.HCl | | 16 | |
| 419 | 3 | 0 | 6-Cl | H | CH₃ | H | 4-CH₃CH₂OPh | 205.8d | 54 | — |
| 420 | 3 | 0 | 6-Cl | H | CH₃ | H | 4-pyridyl | 245.6d | 54 | — |
| 421 | 3 | 0 | H | H | 1,3-di-oxan-5-yl | H | Ph | 131.8 | 36 | — |
| 422 | 3 | 0 | H | H | 1,3-di-oxan-5-yl | H | CH₃CH₂O | 131.8 | 56 | — |
| 423 | 4 | 0 | H | H | 1,3-di-oxan-5-yl | H | Ph.HCl | 157.7 | 59 | — |
| 424 | 4 | 0 | H | H | H | H | H | 222.4 | 53 | — |
| 425 | 3 | 0 | H | H | H | H | H | 124.5 | 54 | — |
| 426 | 2 | 0 | H | H | H | H | H | 114.9 | 54 | — |
| 427 | 4 | 0 | H | H | CH₃ | H | CF₃CF₂CF₂ | | 16 | |
| 428 | 4 | 0 | H | H | H | H | CF₃CF₂CF₂ | | 16 | |
| 429 | 3 | 0 | H | H | CH₃ | H | CF₃CF₂CF₂ | | 16 | |
| 430 | 3 | 0 | H | H | 1,3-di-oxan-5-yl | H | CH₃CH₂CH₂ | 116.1 | 56 | — |
| 431 | 4 | 0 | H | H | 1,3-di-oxan-5-yl | H | CH₃CH₂O | 65.0 | 58 | — |
| 432 | 3 | 0 | H | H | 1,3-di-oxan-5-yl | H | CH₃O | 141.0 | 56 | — |
| 433 | 4 | 0 | H | H | 1,3-di-oxan-5-yl | H | C₂H₅ | 125.7 | 57 | — |
| 434 | 3 | 0 | H | H | 1,3-di-oxan-5-yl | H | C₂H₅ | 118.5 | 36 | — |
| 435 | 4 | 0 | H | H | 1,3-di-oxan-5-yl | H | n-C₃H₇ | 127.1 | 36 | — |

TABLE A-continued

| C | a | n | R₁ | R₂ | R₃ | R₄ | X | m.p. | P | H |
|---|---|---|----|----|----|----|----|------|---|---|
| 436 | 4 | 0 | H | H | 1,3-di-oxan-5-yl | H | CH₃O | 196.3 | 36 | — |

C = Compound #
a = pyridinyl attachment
n = 0 or 1
P = Procedure #
H = Hydrate
m.p. = melting point centigrade (°C.)

TABLE I

*H. Contortus*

| Compound No. | % Clearance P.O. | % Clearance I.P. |
|---|---|---|
| 1 | 99.6 | 100 |
| 2 | 100 | 100 |
| 3 | 100 | 93.7–100 |
| 4 | N.T. | N.T. |
| 5 | N.T. | N.T. |
| 6 | 98.9 | 87.7 |
| 7 | 100 | 100 |
| 8 | 99.9 | N.T. |
| 9 | N.T. | N.T. |
| 10 | 61.9 | N.T. |
| 11 | 99.2 | 99.6 |
| 12 | N.T. | N.T. |
| 13 | N.T. | N.T. |
| 14 | 76.1 | 11.1 |
| 15 | 100 | N.T. |
| 16 | 100 | 100 |
| 17 | 85.9 | 100 |
| 18 | 100 | 94.3 |
| 19 | 99.6 | 86.5 |
| 20 | 96.6 | 100 |
| 21 | N.T. | N.T. |
| 22 | 98.2 | N.T. |
| 23 | 91.1 | 100 |
| 24 | N.T. | N.T. |
| 25 | N.T. | N.T. |
| 26 | 99.8 | 75.0 |
| 27 | 100 | N.T. |
| 28 | 100 | 64.7 |
| 29 | N.T. | N.T. |
| 30 | 100 | 97.1–98.8 |
| 31 | 99.6 | N.T. |
| 31A | 100 | N.T. |
| 32 | N.T. | N.T. |
| 33 | N.T. | N.T. |
| 34 | 97.0 | 93.5 |
| 35 | 99.2 | N.T. |
| 36 | 100 | N.T. |
| 37 | N.T. | N.T. |
| 38 | 22.3 | N.T. |
| 39 | N.T. | N.T. |
| 40 | 98.8 | N.T. |
| 41 | 91.4 | N.T. |
| 42 | 96.9 | 0 |
| 43 | 75.1 | 91.1 |
| 44 | 96.4 | 100 |
| 45 | 82.5 | 12.7 |
| 46 | 96.6 | 86.7 |
| 47 | 20.3 | N.T. |
| 47A | 0 | 2.3 |
| 48 | 100 | 99.7 |
| 48A | N.T. | N.T. |
| 49 | 89.9 | 100 |
| 50 | 29.8 | 12.7 |
| 51 | 97.9 | 100 |
| 52 | 99.6 | N.T. |
| 53 | 7.0 | 0 |
| 54 | 13.3 | N.T. |
| 55 | 75.8 | N.T. |
| 56 | 100 | Toxic |
| 57 | 100 | 19.6 |
| 58 | N.T. | N.T. |
| 59 | N.T. | N.T. |
| 60 | 100 | N.T. |
| 61 | 84.3 | N.T. |
| 62 | N.T. | N.T. |
| 63 | N.T. | N.T. |
| 64 | N.T. | N.T. |
| 65 | N.T. | N.T. |
| 66 | 33.9 | 65.3 |
| 67 | 100 | 100 |
| 68 | 5.7 | 0 |
| 69 | 79.0 | N.T. |
| 70 | 100 | 99.6 |
| 71 | N.T. | N.T. |
| 72 | 98.6 | 99.3 |
| 73 | 100 | 98.9 |
| 74 | Toxic | 98.9 |
| 75 | 99.6 | 100 |
| 76 | 99.3 | 100 |
| 77 | 0 | N.T. |
| 78 | N.T. | 0–69.0 |
| 79 | 99.9 | 0 |
| 80 | 99.9 | N.T. |
| 80A | 75.4 | 68.3 |
| 81 | N.T. | N.T. |
| 82 | N.T. | N.T. |
| 83 | 99.3 | N.T. |
| 84 | 100 | 0–99.6 |
| 85 | 97.9 | 100 |
| 86 | 73.7–99.3 | 0–100 |
| 86A | 100 | 99.8 |
| 87 | N.T. | N.T. |
| 88 | N.T. | N.T. |
| 89 | 98.9 | Toxic |
| 90 | N.T. | N.T. |
| 91 | 21.1–99.6 | 94.5–99.8 |
| 92 | 89.0 | 98.9 |
| 93 | 100 | Toxic |
| 94 | 99.6–100 | 100 |
| 95 | 100 | N.T. |
| 96 | N.T. | N.T. |
| 97 | 73.8–84.6 | 97.6–98.6 |
| 98 | 55.5 | 53.7 |
| 99 | 89.3 | 91.1 |
| 100 | 43.1–70.2 | 46.1–75.1 |
| 101 | 99.9 | 98.9 |
| 102 | 67.4 | 36.6 |
| 103 | 100 | 100 |
| 104 | 85.6 | N.T. |
| 105 | N.T. | 100 |
| 106 | 100 | 98.9 |
| 107 | 100 | N.T. |
| 108 | 96.2 | 82.5 |
| 109 | 80.3 | N.T. |
| 110 | 99.6 | 100 |
| 111 | 98.9 | 100 |
| 112 | 85.5 | 67.0 |
| 113 | 98.8 | 95.7 |
| 114 | 99.9 | 94.5 |
| 115 | 38.4 | 0 |
| 116 | 8.2 | 91.0 |
| 117 | 3.5 | 0 |
| 118 | 100 | 99.7 |
| 119 | 100 | 82.8 |
| 120 | 69.4 | 100 |
| 121 | 100 | 100 |
| 122 | 99.9 | 100 |
| 123 | 96.7 | 0 |
| 124 | 100 | 19.6 |
| 125 | 99.6 | 99.8 |

TABLE I-continued

| | H. Contortus | |
|---|---|---|
| | % Clearance | |
| Compound No. | P.O. | I.P. |
| 126 | 100 | 63.7 |
| 127 | 100 | 24.7 |
| 128 | 100 | 78.7 |
| 129 | 100 | 100 |
| 130 | 98.7 | Toxic |
| 131 | 100 | 99.6 |
| 132 | 94.0 | 97.9 |
| 133 | 100 | N.T. |
| 134 | N.T. | N.T. |
| 135 | N.T. | N.T. |
| 136 | 90.7-100 | N.T. |
| 137 | 75.3 | N.T. |
| 138 | 84.0 | 98.5 |
| 139 | Toxic | Toxic |
| | 98.3++ | Toxic++ |
| 140 | Toxic | Toxic |
| 141 | 76.9 | 100 |
| 142 | 98.6 | 100 |
| 143 | Toxic | N.T. |
| 144 | 100 | 95.4 |
| 145 | 98.9-99.9 | 91.1-98.7 |
| 146 | 85.0 | 99.9 |
| 147 | 100 | Toxic |
| 148 | 100 | 93.2 |
| 149 | 99.6 | 100 |
| 150 | 100 | 100 |
| 151 | 99.6 | 99.6 |
| 152 | 99.9 | 100 |
| 153 | 100 | 100 |
| 154 | 98.1 | 99.1 |
| 155 | 78.1-100 | 87.8 |
| 156 | 100 | 99.6 |
| 157 | 99.6 | 99.6 |
| 158 | 0-49.3 | 0 |
| 159 | N.T. | N.T. |
| 160 | 99.6 | 99.6 |
| 161 | 99.6 | 98.3 |
| 162 | 99.3 | N.T. |
| 163 | N.T. | N.T. |
| 164 | 99.1 | 100 |
| 165 | 97.1 | 100 |
| 166 | 99.6 | 44.5 |
| 167 | 100 | 100 |
| 168 | 100 | 96.7 |
| 169 | N.T. | N.T. |
| 170 | N.T. | N.T. |
| 171 | 99.6 | N.T. |
| 172 | 100 | N.T. |
| 173 | N.T. | N.T. |
| 174 | 100 | N.T. |
| 175 | N.T. | N.T. |
| 176 | N.T. | N.T. |
| 177 | 100 | 99.1 |
| 178 | 100 | N.T. |
| 179 | 99.6 | 82.6 |
| 180 | 99.1 | 15.7 |
| 181 | 100 | 100 |
| 182 | 83.3 | N.T. |
| 183 | 100 | 99.6 |
| 184 | 100 | 100 |
| 185 | N.T. | N.T. |
| 186 | N.T. | N.T. |
| 187 | N.T. | N.T. |
| 188 | N.T. | N.T. |
| 189 | 100 | N.T. |
| 190 | 99.8 | 99.6 |
| 191 | N.T. | N.T. |
| 192 | N.T. | N.T. |
| 193 | 100 | N.T. |
| 194 | 100 | N.T. |
| 195 | 26.8 | 19.6 |
| 196 | N.T. | N.T. |
| 197 | 92.4 | 100 |
| 198 | 100 | Toxic |
| 199 | N.T. | N.T. |
| 200 | Toxic | N.T. |
| 201 | 100 | N.T. |
| 202 | 100 | 100 |
| 203 | 99.1-100 | 100 |
| 204 | Toxic | N.T. |
| 205 | 100 | 94.3 |
| 206 | 98.9 | 87.8 |
| 207 | N.T. | 100 |
| 208 | 76.1 | N.T. |
| 209 | 92.2 | 99.2 |
| 210 | Toxic | N.T. |
| 211 | 85.5 | 99.6 |
| 212 | 96.9 | 64.7 |
| 213 | 76.1 | 50.5 |
| 214 | 99.9 | 99.6 |
| 215 | 98.8 | 84.7-99.8 |
| 216 | N.T. | N.T. |
| 217 | 100 | 100 |
| 218 | N.T. | N.T. |
| 219 | 49.1 | 68.7 |
| 220 | N.T. | N.T. |
| 221 | 91.8 | 97.7 |
| 222 | 98.8 | N.T. |
| 223 | 46.8 | 0 |
| 224 | N.T. | 0-54.0 |
| 225 | N.T. | 99.6 |
| 226 | 100 | 100 |
| 227 | 100 | 0 |
| 228 | 100 | 99.5 |
| 229 | 100 | N.T. |
| 230 | N.T. | N.T. |
| 231 | N.T. | N.T. |
| 232 | N.T. | N.T. |
| 233 | N.T. | N.T. |
| 234 | N.T. | N.T. |
| 235 | N.T. | N.T. |
| 236 | 100 | N.T. |
| 237 | N.T. | N.T. |
| 238 | N.T. | N.T. |
| 239 | 99.8 | 99.9 |
| 240 | N.T. | N.T. |
| 241 | 100 | N.T. |
| 242 | 99.2 | N.T. |
| 243 | 54.9 | 36.4 |
| 244 | 76.5 | 0 |
| 245 | 62.7 | 39.6 |
| 246 | 96.9 | 100 |
| 247 | 100 | 100 |
| 248 | 79.1 | 68.1 |
| 249 | 98.1 | 92.0 |
| 250 | 99.8 | 99.6 |
| 251 | N.T. | N.T. |
| 252 | 69.8 | 41.3 |
| 253 | 90.5 | Toxic |
| 254 | 86.7 | 0 |
| 255 | 87.4 | 0 |
| 256 | 0 | 52.5 |
| 257 | N.T. | N.T. |
| 258 | N.T. | N.T. |
| 259 | N.T. | N.T. |
| 260 | N.T. | N.T. |
| 261 | N.T. | N.T. |
| 262 | 99.6 | 100 |
| 263 | 99.2 | 100 |
| 264 | 100 | Toxic |
| 265 | N.T. | N.T. |
| 266 | N.T. | N.T. |
| 267 | N.T. | N.T. |
| 268 | N.T. | N.T. |
| 269 | N.T. | N.T. |
| 270 | 99.9 | 100 |
| 271 | 100 | N.T. |
| 272 | 98.9 | 97.3 |
| 273 | 100 | 100 |
| 274 | 70.2 | 100 |
| 275 | 99.8 | 100 |
| 276 | 100 | 100 |
| 277 | 99.9 | 100 |
| 278 | 100 | 100 |
| 279 | 99.6 | N.T. |
| 280 | 96.1-97.2 | 85.8-96.6 |

TABLE I-continued

| Compound No. | H. Contortus % Clearance P.O. | I.P. |
|---|---|---|
| 281 | 100 | 0 |
| 282 | 99.6 | 99.6 |
| 283 | 99.6 | N.T. |
| 284 | N.T. | N.T. |
| 285 | N.T. | N.T. |
| 286 | 27.7 | 65.3 |
| 287 | 100 | 99.8 |
| 288 | 99.8 | Toxic |
| 289 | 100 | 100 |
| 290 | 99.7 | N.T. |
| 291 | 98.6 | N.T. |
| 292 | 51.7 | N.T. |
| 293 | N.T. | N.T. |
| 294 | N.T. | N.T. |
| 295 | N.T. | N.T. |
| 296 | N.T. | N.T. |
| 297 | N.T. | N.T. |
| 298 | N.T. | N.T. |
| 299 | N.T. | N.T. |
| 300 | 39.6 | 49.9 |
| 301 | 100 | N.T. |
| 302 | 32.8 | N.T. |
| 303 | 100 | N.T. |
| 304 | 100 | N.T. |
| 305 | 100 | N.T. |
| 306 | 100 | N.T. |
| 307 | 99.3 | N.T. |
| 308 | 100 | N.T. |
| 309 | N.T. | N.T. |
| 310 | 100 | N.T. |
| 311 | 100 | 99.9 |
| 312 | Toxic | N.T. |
| 313 | 100 | N.T. |
| 314 | Toxic | N.T. |
| 315 | 100 | N.T. |
| 316 | 100 | N.T. |
| 317 | 100 | N.T. |
| 318 | 100 | N.T. |
| 319 | 99.3 | N.T. |
| 320 | 92.5 | N.T. |
| 321 | 100 | N.T. |
| 322 | 97.0 | N.T. |
| 323 | 99.3 | N.T. |
| 324 | 100 | N.T. |
| 325 | 100 | N.T. |
| 326 | Toxic | N.T. |
| 327 | 77.6 | N.T. |
| 328 | 100 | N.T. |
| 329 | 100 | N.T. |
| 330 | 100 | N.T. |
| 331 | 10.4 | N.T. |
| 332 | 70.1 | N.T. |
| 333 | 92.5 | N.T. |
| 334 | 100 | N.T. |
| 335 | 0 | N.T. |
| 336 | 92.5 | N.T. |
| 337 | 100 | N.T. |
| 338 | 77.6 | N.T. |
| 339 | 100 | N.T. |
| 340 | N.T. | N.T. |
| 341 | 100 | N.T. |
| 342 | 32.8 | N.T. |
| 343 | N.T. | N.T. |
| 344 | N.T. | N.T. |
| 345 | N.T. | N.T. |
| 346 | 97.8 | N.T. |
| 347 | 100 | N.T. |
| 348 | 77.6 | N.T. |
| 349 | 89.6 | 99.8 |
| 350 | N.T. | N.T. |
| 351 | 100 | 100 |
| 352 | 99.9 | N.T. |
| 353 | N.T. | N.T. |
| 354 | 100 | N.T. |
| 355 | 3.0* | N.T. |
| 356 | Toxic | N.T. |
| 357 | Toxic | N.T. |
| 358 | 100 | N.T. |
| 359 | N.T. | N.T. |
| 360 | 99-3-100 | N.T. |
| 361 | N.T. | N.T. |
| 362 | 100 | N.T. |
| 363 | 99.3 | N.T. |
| 364 | 100 | N.T. |
| 365 | 100 | N.T. |
| 366 | 100 | N.T. |
| 367 | 100 | N.T. |
| 368 | 100 | N.T. |
| 369 | 85.1 | N.T. |
| 370 | 100 | N.T. |
| 371 | 85.1 | N.T. |
| 372 | 62.7** | N.T. |
| 373 | 92.5 | N.T. |
| 374 | 92.5 | N.T. |
| 375 | 55.2 | N.T. |
| 376 | N.T. | N.T. |
| 377 | 77.6 | N.T. |
| 378 | 100 | N.T. |
| 379 | 92.5 | N.T. |
| 380 | 100 | N.T. |
| 381 | 92.5 | N.T. |
| 382 | 92.5 | N.T. |
| 383 | 92.5 | N.T. |
| 384 | 55.2 | N.T. |
| 385 | 100 | N.T. |
| 386 | 85.1 | N.T. |
| 387 | N.T. | N.T. |
| 388 | 77.6 | N.T. |
| 389 | 85.1 | N.T. |
| 390 | N.T. | N.T. |
| 391 | $100^X$ | N.T. |
| 392 | 47.8 | N.T. |
| 393 | 85.1 | N.T. |
| 394 | 97.8 | N.T. |
| 395 | 92.5 | N.T. |
| 396 | $100^+$ | N.T. |
| 397 | 62.7 | N.T. |
| 398 | 0 | N.T. |
| 399 | 100 | N.T. |
| 400 | 85.1 | N.T. |
| 401 | 93.3 | N.T. |
| 402 | 70.1 | N.T. |
| 403 | 3.0 | N.T. |
| 404 | N.T. | N.T. |
| 405 | 62.7 | N.T. |
| 406 | N.T. | N.T. |
| 407 | N.T. | N.T. |
| 408 | 55.2 | N.T. |
| 409 | Toxic | N.T. |
| 410 | 85.1 | N.T. |
| 411 | 92.5 | N.T. |
| 412 | 100 | N.T. |
| 413 | 92.5 | N.T. |
| 414 | 99.3 | N.T. |
| 415 | 85.1 | N.T. |
| 416 | 85.1 | N.T. |
| 417 | 0 | N.T. |
| 418 | N.T. | N.T. |
| 419 | N.T. | N.T. |
| 420 | N.T. | N.T. |
| 421 | 100 | N.T. |
| 422 | 100 | N.T. |
| 423 | 100 | N.T. |
| 424 | 100 | N.T. |
| 425 | 95.5 | N.T. |
| 426 | 40.3 | N.T. |
| 427 | N.T. | N.T. |
| 428 | N.T. | N.T. |
| 429 | N.T. | N.T. |
| 430 | 100 | N.T. |
| 431 | 100 | N.T. |
| 432 | 98.5 | N.T. |
| 433 | 100 | N.T. |
| 434 | 98.5 | N.T. |
| 435 | 100 | N.T. |

TABLE I-continued

| Compound No. | H. Contortus % Clearance | |
|---|---|---|
| | P.O. | I.P. |
| 436 | 100 | N.T. |

++50 mg/kg
*95 mg/kg
**60 mg/kg

TABLE II

Percentage Clearance of Adult Worms by Species (100 mg/kg)

| Cmp. # | Route | H. c. | Ost. c. | T. a. | T. c. | C. c. | N. s. | Str. p. | Trich. o. | Oes. v. | M. e. |
|---|---|---|---|---|---|---|---|---|---|---|---|
| 144 | Oral | 100 | 100 | 100 | 41.4 | 100 | 100 | 61.5 | 0 | 100 | 80 |
| 144 | IP | 96.7 | 96.0 | 91.1 | 17.1 | 100 | 97.5 | 30.8 | 50.0 | 100 | 40 |
| 136 | Oral | 98.2 | 0 | 100 | 50.0 | 55.6 | 0 | 15.4 | 0 | | |
| 155 | Oral | 91.2 | 85.9 | 0 | 100 | 71.8 | 97.6 | 0 | 41.2 | 0 | + |
| 72 | IP | 98.3 | 93.9 | 44.9 | 19.3 | 31.9 | 93.8 | 70.7 | 55.6 | 83.3 | |
| 91 | Oral | 98.8 | 59.1 | 100 | 83.3 | 0 | 73.4 | | 0 | 100 | — |
| 91 | IP | 97.1 | 86.4 | 100 | 0 | 100 | 50.0 | | 100 | 100 | — |
| 86 | Oral | 93.6 | 100 | 100 | 55.6 | 100 | 5.6 | | 100 | 100 | — |
| 86 | IP | 94.2 | 88.6 | 35.0 | 0 | 100 | 0 | | 0 | 63.6 | — |
| 3 | Oral | 100 | | 96.6 | 34.3 | | 79.4 | | 3.2 | 100 | |
| 3 | Oral | 98.3 | 94.2 | 13.9 | 27.4 | 16.4 | 38.6 | 75.8 | 87.1 | 0 | |
| 30 | Oral | 100 | 18.5 | | | 0 | 84.4 | | 100 | | 85.0 |
| 30 | IP | 100 | 0 | | | 0 | 42.2 | | 100 | | 50.0 |
| 183 | Oral | 40.0 | 19.9 | | | 34.5 | 75.6 | | 100 | | 35.0 |
| 183 | IP | 40.0 | 48.9 | | | 85.5 | 93.3 | | 100 | | 35.0 |
| 291 | IP | 91.1 | 82.1 | 77.8 | 0 | 14.7 | 63.3 | 20.5 | 0 | | — |

Definitions:
H. c. = *Haemonchus contortus*
Ost. c. = *Ostertagia circumcincta*
T. a. = *Trichostrongylus axei*
T. c. = *Trichostrongylus colubriformis*
C. c. = *Cooperia curticei*
N. s. = *Nematodirus spathiger*
Str. p. = *Strongyloides papillosus*
Trich. o. = *Trichuris ovis*
Oes. v. = *Oesophagostomum venulosum*
M. e. = *Moniezia expansa*

$x$88 mg/kg
+84 mg/kg
N.T. = not tested
_ - _, means the compound was tested two or more times and the extreme values reported (for example, 0–97.6)
I.P. = Parenteral administration
P.O. = Oral administration
Toxic = Death within 24 hours post-treatment

TABLE IIA

Percentage Clearance of Adult Worms by Species or Genera (100 mg/kg)

| Cmd. # | Route | H.c. | Ost. Spp. | T. a. | T. c. | C. Spp. | N. Spp. | Str. Spp. | Trich. Spp. | Oes. Spp. |
|---|---|---|---|---|---|---|---|---|---|---|
| 2 | PO | 100 | 99.2 | 100 | 44.4 | — | 88.3 | 15.0 | 0 | 100 |
| 144 | PO | 100 | 100 | 100 | 41.4 | 100 | 100 | 61.5 | 0 | 100 |
| | IP | 96.7 | 96.0 | 91.1 | 17.1 | 100 | 97.5 | 30.8 | 50.0 | 100 |
| 153 | PO | 98.9 | 61.5 | 65.0 | 0 | — | 50.0 | 0 | 0 | 55.6 |
| | IP | 95.9 | 97.0 | 100 | 83.3 | — | 75.0 | 66.7 | 78.1 | 100 |
| 16 | PO | 94.6 | 90.4 | 100 | 50.0 | — | 64.9 | 0 | 61.1 | 98.5 |
| 275 | PO | 100 | 100 | — | 58.3 | — | 92.7 | 100 | 0 | 100 |
| | IP | 100 | 82.1 | — | 100 | — | 100 | 79.2 | 0 | 100 |
| 160 | PO | 97.8 | 90.0 | 85.7 | 52.8 | — | 74.9 | — | 0 | 88.2 |
| 203 | PO | 99.5 | 79.6 | — | 76.7 | 0 | 83.6 | — | 0 | 82.5 |
| | IP | 99.3 | 66.3 | — | 33.3 | 0 | 69.1 | — | 42.3 | 87.5 |

TABLE IIA-continued

| | | Percentage Clearance of Adult Worms by Species or Genera (100 mg/kg) | | | | | | | | |
|---|---|---|---|---|---|---|---|---|---|---|
| Cmd. # | Route | H.c. | Ost. Spp. | T. a. | T. c. | C. Spp. | N. Spp. | Str. Spp. | Trich. Spp. | Oes. Spp. |
| 73 | PO | 99.9 | 97.5 | 79.2 | 73.0 | 5.6 | 94.9 | 53.8 | — | 86.7 |

Definitions:
H. c. = *Haemonchus contortus*
Ost. Spp. = *Ostertagia* spp.
T. a. = *Trichostrongylus axei*
T. c. = *Trichostrongylus colubriformis*
C. Spp. = *Cooperia* spp.
N. Spp. = *Nematodirus* spp.
Str. Spp. = *Strongyloides* spp.
Trich. Spp. = *Trichuris* spp.
Oes. Spp. = *Oesophagostomum* spp.

CHART A
SCHEME A:

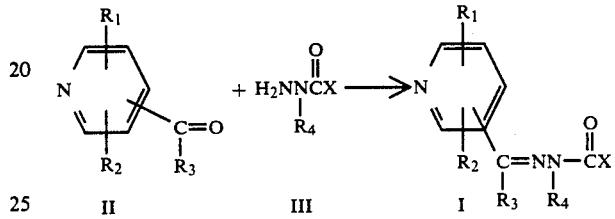

Scheme B:

TABLE III

| | | | | Compound No. 144 - Multi-Dose Study | | | | | | | |
|---|---|---|---|---|---|---|---|---|---|---|---|
| Compound No. | Dosage (mg/kg) | Route | H. contortus | O. circumcincta | T. axei | T. colubriformis | C. curticei | N. spathiger | S. papillosus | T. ovis | O. venulosum | M. expansa |
| 144 | 100 | oral | 0 (100) | 0 (100) | 0 (100) | 695 (41.4) | 0 (100) | 0 (100) | 5 (61.5) | 4 (0) | 0 (100) | 1 (80.0) |
| 144 | 50 | Oral | 16 (99.4) | 250 (57.8) | 10 (82.1) | 1,766 (0) | 10 (28.6) | 39 (80.3) | 9 (30.8) | 2 (0) | 1 (83.3) | 0*(100) |
| 144 | 25 | Oral | 4 (99.8) | 84 (85.8) | 4 (92.9) | 1,307 (0) | 2 (85.7) | 204 (0) | 19 (0) | 2 (0) | 2 (66.7) | 2 (60.0) |
| 144 | 100 | Parenteral | 83 (96.7) | 24 (96.0) | 5 (91.1) | 982 (17.1) | 0 (100) | 5 (97.5) | 9 (30.8) | 1 (50.0) | 0 (100) | 3 (40.0) |
| 144 | 50 | Parenteral | 14 (99.4) | 87 (85.3) | 8 (85.7) | 828 (30.1) | 8 (42.9) | 56 (71.1) | 11 (15.4) | 2 (0) | 3 (50 0) | 2 (60.0) |
| 144 | 25 | Parenteral | 8 (99.7) | 161 (72.8) | 12 (78.6) | 2,524 (0) | 0 (100) | 108 (45.4) | 6 (53.8) | 0* (100) | 4 (33.3) | 3 (40.0) |
| Levamisole Hydrochloride | 8 | Oral | 0 (100) | 0 (100) | 0 (100) | 7 (99.4) | 0 (100) | 0 (100) | 0 (100) | 0* (100) | 0 (100) | 2 (60.0) |
| Non-Treated | — | — | 2,487 | 593 | 56 | 1,185 | 14 | 198 | 13 | 2 | 6 | 5 |

Mean numbers of worms/species recovered at necropsy and (% clearance+) by species for each treatment
*Worms were recovered; however, the mean did not round off to 1.
+% clearance =
(Mean # of worms recovered/species/nontreated control sheep) − (Mean # worms recovered/species/treated sheep) × 100 / Mean # of worms recovered/species/nontreated control sheep

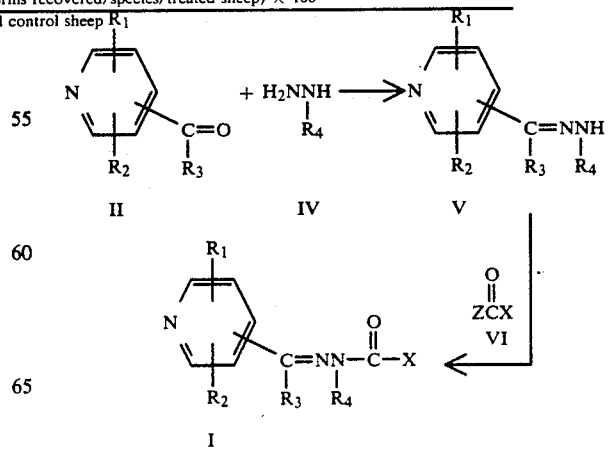

Z is a halogen atom or other active group, for example, an anhydride.

Scheme C:

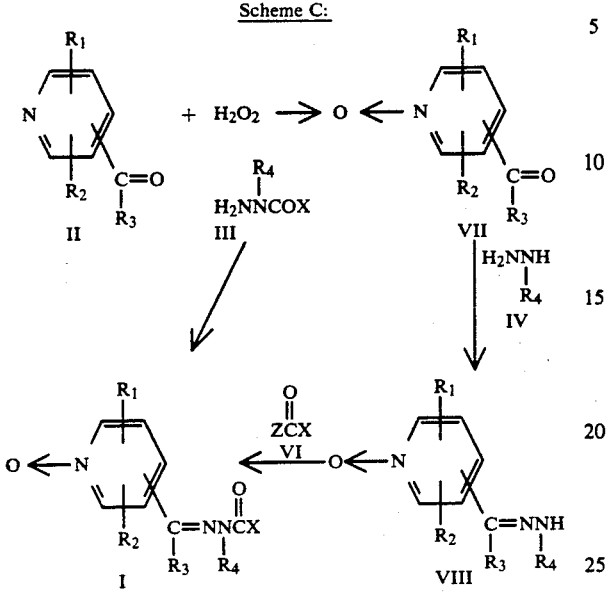

FORMULAE

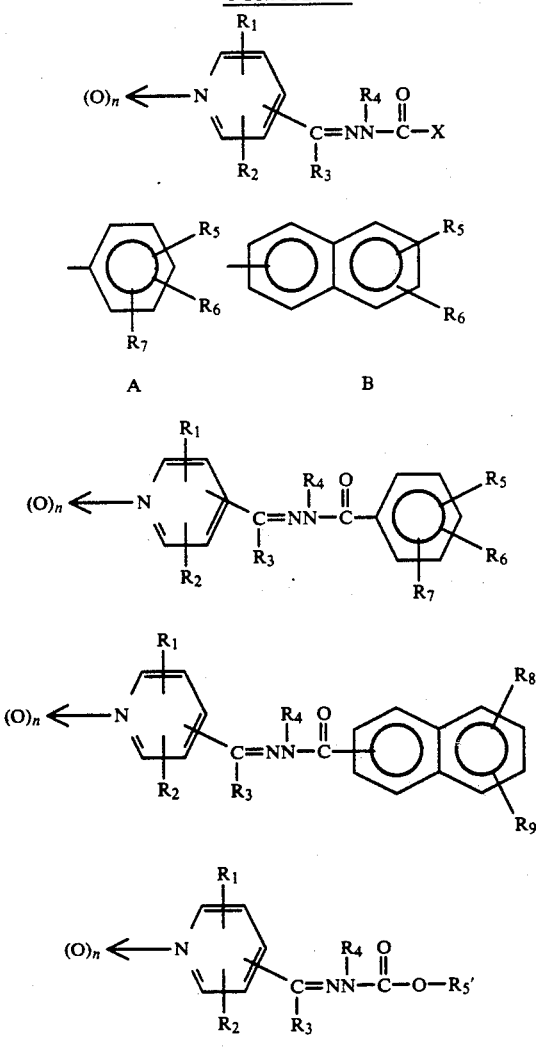

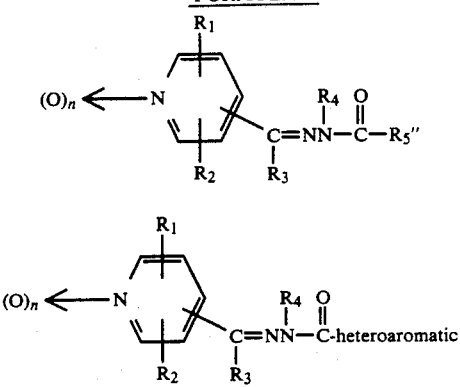

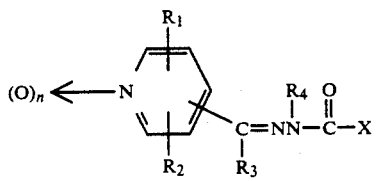

We claim:

1. A compound, hydrate thereof or pharmaceutically acceptable salt thereof of the formula wherein X is selected from (o)$C_1$-$C_6$ alkoxy; (p)diphenylmethoxy; (q)cyclo($C_3$-$C_6$)alkyloxy optionally substituted with one or two $C_1$-$C_3$ alkyl; (r)phenoxy optionally substituted with one, 2 or 3 $C_1$-$C_4$ alkyl, $C_1$-$C_4$ alkoxy, halo, or trifluoromethyl; and (s)benzyloxy optionally substituted with one, 2 or 3 $C_1$-$C_4$ alkyl, $C_1$-$C_4$ alkoxy, halo, or trifluoromethyl; with the proviso that when a 2-pyridinyl acylhydrazone and $R_1$, $R_2$, $R_4$ are hydrogen, $R_3$ is not benzyl;

wherein $R_1$ and $R_2$, being the same or different, are hydrogen; hydroxy; $C_1$-$C_4$ alkyl; $C_1$-$C_3$ alkoxy; $C_1$-$C_3$ alkylthio; halo or trifluoromethyl;

wherein $R_3$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl ($C_1$-$C_3$)alkyl optionally substituted with one, 2 or 3 $C_1$-$C_4$ alkyl, halo, trifluoromethyl, or $C_1$-$C_3$ alkoxy; or 1,3-dioxacyclohexan-5-yl;

wherein $R_4$ is hydrogen; $C_1$-$C_2$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2, or 3 $C_1$-$C_4$ alkyl, halo, trifluoromethyl, or $C_1$-$C_3$ alkoxy; and wherein n is zero or one;

other than:
methyl(2-pyridinylmethylene)carbazate;
ethyl(2-pyridinylmethylene)carbazate.
ethyl(4-pyridinylmethylene)carbazate; and
ethyl[1-(2-pyridinyl)ethylidene]carbazate.

2. A compound, hydrate or pharmaceutically acceptable salt thereof, according to claim 1 selected from the group consisting of
ethyl [1-(4-pyridinyl)ethylidene)carbazate (Cpd #72);
ethyl (3-pyridinylmethylene)carbazate (Cpd #74);

1,1-dimethylethyl [1-(4-pyridinyl)ethylidene]carbazate (Cpd #76);
benzyl [1-(4-pyridinyl)ethylidene]carbazate (Cpd #79);
diphenylmethyl [1-(4-pyridinyl)ethylidene]carbazate (Cpd #80);
diphenylmethyl [1-(2-pyridinyl)ethylidene]carbazate (Cpd #80A);
methyl(4-pyridinylmethylene)carbazate hydrate (Cpd #83);
benzyl (4-pyridinylmethylene)carbazate (Cpd #84);
methyl [1-(4-pyridinyl)ethylidene]carbazate (Cpd #85);
diphenylmethyl (4-pyridinylmethylene)carbazate (Cpd #86);
methyl [1-(3-pyridinyl)ethylidene]carbazate (Cpd #89);
1,1-dimethylethyl [1-(4-pyridinyl)propylidene]carbazate (Cpd #91);
benzyl [1-(4-pyridinyl)propylidene]carbazate (Cpd #92);
methyl [1-(4-pyridinyl)propylidene]carbazate (Cpd #93);
phenyl [1-(4-pyridinyl)ethylidene]carbazate (Cpd #94);
phenyl [1-(4-pyridinyl)ethylidene]carbazate monohydrochloride (Cpd #95);
5-methyl-2-(1-methylethyl)cyclohexyl[1-(4-pyridinyl)ethylidene]carbazate (Cpd #97);
ethyl [1-(4-pyridinyl)pentylidene]carbazate (Cpd #99);
phenyl [1-(4-pyridinyl)butylidene]carbazate monohydrochloride (Cpd #100);
phenyl (4-pyridinylmethylene)carbazate monohydrochloride (Cpd #101);
1,1-dimethylethyl [1-(3-pyridinyl)propylidene]carbazate (Cpd #103);
ethyl [1-(b 2- pyridinyl)propylidene]carbazate (Cpd #105);
1,1-dimethylethyl [1-(2-pyridinyl)propylidene]carbazate (Cpd #106);
ethyl [1-(3-pyridinyl)propylidene]carbazate (Cpd #107);
1,1-dimethylethyl [1-(4-pyridinyl)butylidene]carbazate (Cpd #108);
ethyl [1-(4-pyridinyl)ethylidene]carbazate 1-oxide (Cpd #109);
ethyl [1-(4-pyridinyl)butylidene]carbazate (Cpd #110);
methyl [1-(4-pyridinyl)ethylidene]carbazate 1-oxide (Cpd #111);
phenyl [1-(4-pyridinyl)butylidene]carbazate 1-oxide (Cpd #112);
1,1-dimethylethyl [1-(4-pyridinyl)butylidene]carbazate 1-oxide (Cpd #113);
ethyl [1-(4-pyridinyl)butylidene]carbazate 1-oxide (Cpd #114);
1,1-dimethylethyl [3-methyl-1-(4-pyridinyl)butylidene]carbazate (Cpd #116);
phenyl [1-(4-pyridinyl)ethylidene]carbazate 1-oxide monohydrochloride (Cpd #118);
benzyl [1-(4-pyridinyl)ethylidene]carbazate 1-oxide hydrate (Cpd #119);
1,1-dimethylethyl [1-(4-pyridinyl)ethylidene]carbazate 1-oxide (Cpd #120);
4-methoxybenzyl (3-pyridinylmethylene)carbazate (Cpd #128);
4-methoxybenzyl (4-pyridinylmethylene)carbazate (Cpd #129);
4-methoxybenzyl [1-(3-pyridinyl)ethylidene]carbazate monohydrate (Cpd #130);
4-methoxybenzyl [1-(4-pyridinyl)ethylidene]carbazate (Cpd #131);
ethyl [(6-methyl-2-pyridinyl)methylene]carbazate hydrate (Cpd #132);
4-methoxybenzyl (2-pyridinylmethylene)carbazate (Cpd #133);
ethyl [1-(6-methyl-3-pyridinyl)ethylidene]carbazate (Cpd #332);
1,1-dimethylethyl[1-(6-methyl-3-pyridinyl)ethylidene]carbazate (Cpd #333);
phenyl[1-(6-methyl-3-pyridinyl)ethylidene]carbazate monohydrochloride (Cpd #334);
methyl [1-(3-chloro-4-pyridinyl)ethylidene]carbazate (Cpd #396);
ethyl [(1,3-dioxan-5-yl)-3-pyridinylmethylene]carbazate (Cpd #422);
ethyl [(1,3-dioxan-5-yl)-4-pyridinylmethylene]carbazate (Cpd #431);
methyl [(1,3-dioxan-5-yl)-3-pyridinylmethylene]carbazate (Cpd #432); and
methyl [(1,3-dioxan-5-yl)-4-pyridinylmethylene]carbazate (Cpd #436).

* * * * *